(12) United States Patent
Melarkode et al.

(10) Patent No.: US 8,524,233 B2
(45) Date of Patent: Sep. 3, 2013

(54) MONOCLONAL ANTIBODY AND A METHOD THEREOF

(75) Inventors: Ramakrishnan Melarkode, Karnataka (IN); Pradip Nair, Karnataka (IN); Sundaraj David Rajkumar, Tamilnadu (IN); Kedarnath Nanjund Sastry, Karnataka (IN); Monalisa Chatterji, Karnataka (IN); Laxmi Adhikary, Karnataka (IN); Hema Balasubramanian, Karnataka (IN); Jose Enrique Montero Casimiro, Cuba (CU); Josefa Lombardero Valladares, Cuba (CU); Rolando Perez Rodriguez, Cuba (CU)

(73) Assignee: Biocon Limited & Centro de Immunologia Molecular, Cuba (IN)

( * ) Notice: Subject to any disclaimer, the term of this patent is extended or adjusted under 35 U.S.C. 154(b) by 74 days.

(21) Appl. No.: 12/921,544

(22) PCT Filed: Sep. 4, 2008

(86) PCT No.: PCT/IN2008/000562
§ 371 (c)(1),
(2), (4) Date: Sep. 8, 2010

(87) PCT Pub. No.: WO2009/113083
PCT Pub. Date: Sep. 17, 2009

(65) Prior Publication Data
US 2011/0002939 A1 Jan. 6, 2011

(30) Foreign Application Priority Data
Mar. 14, 2008 (IN) .............................. 650/CHE/2008

(51) Int. Cl.
*A61K 39/395* (2006.01)
(52) U.S. Cl.
USPC .............. 424/144.1; 530/388.73; 530/388.75; 530/388.8

(58) Field of Classification Search
None
See application file for complete search history.

(56) References Cited

U.S. PATENT DOCUMENTS

| 5,712,120 | A | 1/1998 | Rodriguez et al. |
| 6,572,857 | B1 | 6/2003 | Casimiro et al. |
| 2002/0187526 | A1 * | 12/2002 | Ruben et al. .................. 435/69.5 |

FOREIGN PATENT DOCUMENTS

| WO | WO 9847531 A2 * | 10/1998 |
| WO | WO 01/70984 A2 | 9/2001 |
| WO | WO 01/91793 A1 | 12/2001 |
| WO | WO 2005/080432 A2 | 9/2005 |
| WO | WO 2008/077355 A1 | 7/2008 |

OTHER PUBLICATIONS

Heldin et al., Cell. Jan. 27, 1995;80(2):213-23.*
Goldsby et al., Immunology, 2002, Freeman Press, pp. 290-291.*
Chen et al., J Immunol. Dec. 1, 2002;169(11):6530-8.*
Horwitz et al., Arthritis Rheum. May 1998;41(5):838-44.*
Fuss et al., The Journal of Clinical Investigation, vol. 113 No. 10 May 2004, p. 1490-1497.*
Mavilia et al., Am J Pathol. Dec. 1997;151(6):1751-8.*
Roep et al., Nat Rev Immunol. Dec. 2004;4(12):989-97.*
Bart Roep, Ann. N.Y. Acad. Sci. 1103: 1-10 (2007).*
Roque-Navarro et al., "Humanization of Predicted T-Cell Epitopes Reduces the Immunogenicity of Chimeric Antibodies: New Evidence Supporting a Simple Method," *Hybridoma and Hybridomics* (2003), 22(4):245-257.

* cited by examiner

*Primary Examiner* — Zachary Skelding
(74) *Attorney, Agent, or Firm* — Marianne Fuierer; Moore & Van Allen, PLLC

(57) ABSTRACT

The present invention relates to a humanized IgG1 isotype anti-CD6 antibody (T1h) that binds to the Scavenger receptor cysteine-rich (SRCR) domain 1 (D1) of CD6 present on the surface of thymic epithelial cells, monocytes, activated T cells and a variety of other cells types.

6 Claims, 34 Drawing Sheets

Figure 2:
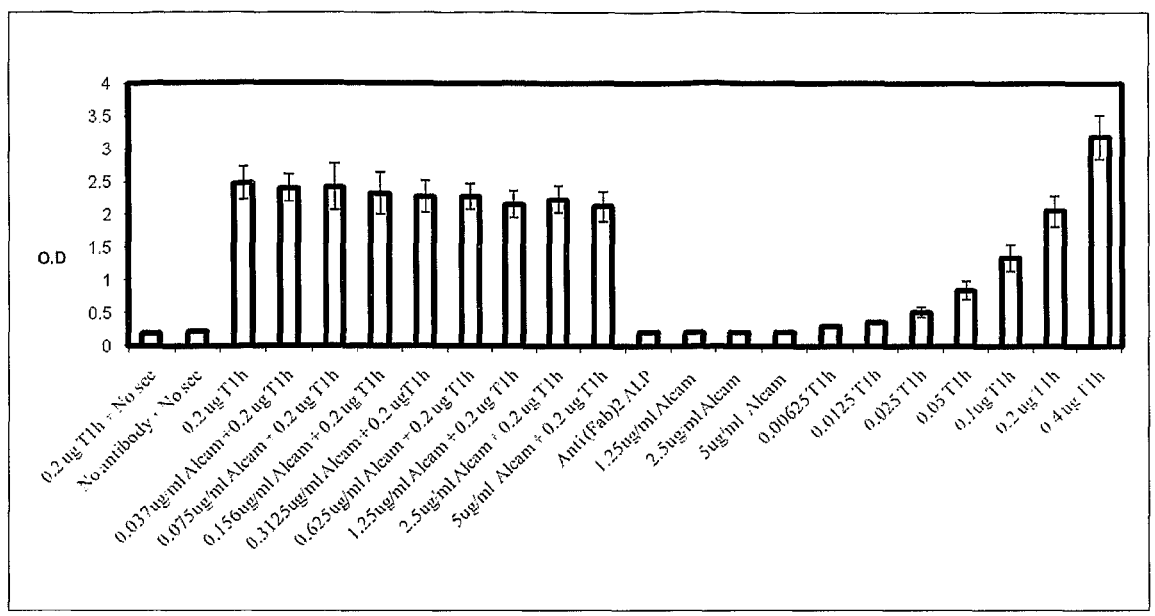

VH sequence:

GAAGTGCAGCTGGTGGAGTCTGGGGGAGGCTTAGTGAAGCCTGGAGGGTCCCTGAAACTCTCC
TGTGCAGCCTCTGGATTCAAGTTTAGTAGATATGCCATGTCTTGGGTTCGCCAGGCTCCGGGGA
AGAGGCTGGAGTGGGTCGCAACCATTAGTAGTGGTGGTAGTTACATCTACTATCCAGACAGTG
TGAAGGGTCGATTCACCATCTCCAGAGACAATGTCAAGAACACCCTGTATCTGCAAATGAGCA
GTCTGAGGTCTGAGGACACGGCCATGTATTACTGTGCAAGACGAGATTACGACCTGGACTACT
TTGACTCCTGGGGCCAAGGCACCCTTGTCACCGTCTCCTCA

Vk sequence:

GACATCCAGATGACCCAGTCTCCATCCTCCCTGTCTGCATCGGTGGGAGACAGAGTCACTATC
ACTTGCAAGGCGAGTCGGGACATTAGAAGCTATTTAACCTGGTACCAGCAGAAACCAGGGAA
AGCTCCTAAGACCCTGATCTATTATGCAACAAGCTTGGCAGATGGGGTCCCGTCGAGATTCAG
TGGCAGTGGATCTGGGCAAGATTATTCTCTCACCATCAGCAGCCTGGAGTCTGACGATACAGC
AACTTACTACTGTCTACAACATGGTGAGAGTCCATTCACGCTCGGCTCGGGGACCAAGCTGGA
AATCAAA

Figure 1a

VH sequence:

EVQLVESGGGLVKPGGSLKLSCAASGFKFSRYAMSWVRQAPGKRLEW
VATISSGGSYIYYPDSVKGRFTISRDNVKNTLYLQMSSLRSEDTAMYY
CARRDYDLDYFDSWGQGTLVTVSS

VK sequence:

DIQMTQSPSSLSASVGDRVTITCKASRDIRSYLTWYQQKPGKAPKTLI
YYATSLADGVPSRFSGSGSGQDYSLTISSLESDDTATYYCLQHGESPFT
LGSGTKLEIK

Figure 1b

DIQMTQSPSSLSASVGDRVTITCKASRDIRSYLTWYQQKP
DIQMTQSPSSLSASVGDRVTITCKASRDIRSYLTWYQQKP
DIQMTQSPSSLSASVGDRVTITCKASRDIRSYLTWYQQKP

GKAPKTLIYYATSLADGVPSRFSGSGSGQDYSLTISSLESD
GKAPKTLIYYATSLADGVPSRFSGSGSGQDYSLTISSLESD
GKAPKTLIYYATSLADGVPSRFSGSGSGQDYSLTISSLESD

DTATYYCLQHGESPFTFGSGTKLEIKRA  EP0807125 B1,
DTATYYCLQHGESPFTFGSGTKLEIK - -  Translated Nucleotide sequence from Genomic DNA
DTATYYCLQHGESPFTLGSGTKLEIK - -  Amino acid sequence

Figure 1c

|   | 1 | 2 | 3 | 4 | 5 | 6 | 7 | 8 | 9 | 10 | 11 | 12 |
|---|---|---|---|---|---|---|---|---|---|---|---|---|
| A | CD3 1ug/ml | CD3 1ug/ml | CD3 1ug/ml | CD3 1ug/ml | CD3 1ug/ml+T1h | CD3 1ug/ml+T1h | CD3 1ug/ml+T1h | CD3 1ug/ml+T1h | CD3 1ug/ml+Alcam | CD3 1ug/ml+Alcam | CD3 1ug/ml+Alcam | CD3 1ug/ml+Alcam |
| B | CD3 0.5ug/ml | CD3 0.5ug/ml | CD3 0.5ug/ml | CD3 0.5ug/ml | CD3 0.5ug/ml+T1h | CD3 0.5ug/ml+T1h | CD3 0.5ug/ml+T1h | CD3 0.5ug/ml+T1h | CD3 0.5ug/ml+alcam | CD3 0.5ug/ml+alcam | CD3 0.5ug/ml+alcam | CD3 0.5ug/ml+alcam |
| C | CD3 0.25ug/ml | CD3 0.25ug/ml | CD3 0.25ug/ml | CD3 0.25ug/ml | CD3 0.25ug/ml+T1h | CD3 0.25ug/ml+T1h | CD3 0.25ug/ml+T1h | CD3 0.25ug/ml+T1h | CD3 0.25ug/ml+Alcam | CD3 0.25ug/ml+Alcam | CD3 0.25ug/ml+Alcam | CD3 0.25ug/ml+Alcam |
| D | CD3 0.125ug/ml | CD3 0.125ug/ml | CD3 0.125ug/ml | CD3 0.125ug/ml | CD3 0.125ug/ml | CD3 0.125ug/ml | CD3 0.125ug/ml | CD3 0.125ug/ml | CD3 0.125ug/ml | CD3 0.125ug/ml | CD3 0.125ug/ml | CD3 0.125ug/ml |
| E | CD3 0.625ug/ml | CD3 0.625ug/ml | CD3 0.625ug/ml | CD3 0.625ug/ml | CD3 0.625ug/ml+T1h | CD3 0.625ug/ml+T1h | CD3 0.625ug/ml+T1h | CD3 0.625ug/ml+T1h | CD3 0.625ug/ml Alcam | CD3 0.625ug/ml Alcam | CD3 0.625ug/ml Alcam | CD3 0.625ug/ml Alcam |
| F | No Anitbody | No Anitbody | No Anitbody | T1h 1ug/ml; | T1h 1ug/ml; | T1h 1ug/ml; | hR3 1ug/ml | hR3 1ug/ml | hR3 1ug/ml | alcam 1ug/ml | alcam 1ug/ml | alcam 1ug/ml |
| G | No Anitbody | No Anitbody | No Anitbody | T1h 1ug/ml; | T1h 1ug/ml; | T1h 1ug/ml; | hR3 1ug/ml | hR3 1ug/ml | hR3 1ug/ml | alcam 1ug/ml | alcam 1ug/ml | alcam 1ug/ml |
| H |   |   |   |   |   |   |   |   |   |   |   |   |

Figure 18

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   | PBL | PBL | PBL | PBL | PBL | PBL+DC+T1h40 | PBL+DC+T1h40 | PBL+DC+T1h40 | PBL+DC+T1h40 | PBL+DC+T1h40 |   |
| C |   | DC | DC | DC | DC | DC | PBL+DC+T1h20 | PBL+DC+T1h20 | PBL+DC+T1h20 | PBL+DC+T1h20 | PBL+DC+T1h20 |   |
| D |   | PBL(M)+DC | PBL(M)+DC | PBL(M)+DC | PBL(M)+DC | PBL(M)+DC | PBL+DC+T1h10 | PBL+DC+T1h10 | PBL+DC+T1h10 | PBL+DC+T1h10 | PBL+DC+T1h10 |   |
| E |   | PBL+DC | PBL+DC | PBL+DC | PBL+DC | PBL+DC | PBL+DC+Pim100 | PBL+DC+Pim100 | PBL+DC+Pim100 | PBL+DC+Pim100 | PBL+DC+Pim100 |   |
| F |   | PBL+DC+hR3 40 | PBL+DC+hR3 40 | PBL+DC+hR3 40 | PBL+DC+hR3 40 | PBL+DC+hR3 40 | PBL+DC+Pim50 | PBL+DC+Pim50 | PBL+DC+Pim50 | PBL+DC+Pim50 | PBL+DC+Pim50 |   |
| G |   | PBL+DC+hR3 20 | PBL+DC+hR3 20 | PBL+DC+hR3 20 | PBL+DC+hR3 20 | PBL+DC+hR3 20 | PBL+DC+Pim25 | PBL+DC+Pim25 | PBL+DC+Pim25 | PBL+DC+Pim25 | PBL+DC+Pim25 |   |
| H |   |   |   |   |   |   |   |   |   |   |   |   |

Figure 29

SEQUENCE LISTING

```
<160> NUMBER OF SEQ ID NOS: 5

<210> SEQ ID NO 1
<211> LENGTH: 119
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Leu Gly Ser Gly Thr Lys Leu Glu Ile Lys
```

<210> SEQ ID NO 3
<211> LENGTH: 357
<212> TYPE: DNA
<213> ORGANISM: Artificial Sequence
<220> FEATURE:
<223> OTHER INFORMATION: Synthetic construct
<220> FEATURE:
<221> NAME/KEY: exon
<222> LOCATION: (1)..(357)

<400> SEQUENCE: 3

```
gaa gtg cag ctg gtg gag tct ggg gga ggc tta gtg aag cct gga ggg      48
Glu Val Gln Leu Val Glu Ser Gly Gly Gly Leu Val Lys Pro Gly Gly
1               5                   10                  15 tcc ctg aaa ctc tcc tgt gca gcc tct gga ttc aag ttt agt aga tat      96
Ser Leu Lys Leu Ser Cys Ala Ala Ser Gly Phe Lys Phe Ser Arg Tyr
            20                  25                  30 gcc atg tct tgg gtt cgc cag gct ccg ggg aag agg ctg gag tgg gtc     144
Ala Met Ser Trp Val Arg Gln Ala Pro Gly Lys Arg Leu Glu Trp Val
        35                  40                  45 gca acc att agt agt ggt ggt agt tac atc tac tat cca gac agt gtg     192
Ala Thr Ile Ser Ser Gly Gly Ser Tyr Ile Tyr Tyr Pro Asp Ser Val
    50                  55                  60 aag ggt cga ttc acc atc tcc aga gac aat gtc aag aac acc ctg tat     240
Lys Gly Arg Phe Thr Ile Ser Arg Asp Asn Val Lys Asn Thr Leu Tyr
65                  70                  75                  80 ctg caa atg agc agt ctg agg tct gag gac acg gcc atg tat tac tgt     288
Leu Gln Met Ser Ser Leu Arg Ser Glu Asp Thr Ala Met Tyr Tyr Cys
                85                  90                  95 gca aga cga gat tac gac ctg gac tac ttt gac tcc tgg ggc caa ggc     336
Ala Arg Arg Asp Tyr Asp Leu Asp Tyr Phe Asp Ser Trp Gly Gln Gly
            100                 105                 110 acc ctt gtc acc gtc tcc tca                                         357
Thr Leu Val Thr Val Ser Ser
        115
```

<210> SEQ ID NO 4
<211> LENGTH: 318
<212> TYPE: DNA
<213> ORGANISM: Artificial Sequence
<220> FEATURE:
<223> OTHER INFORMATION: Synthetic Construct
<220> FEATURE:
<221> NAME/KEY: exon
<222> LOCATION: (1)..(318)

<400> SEQUENCE: 4

```
gac atc cag atg acc cag tct cca tcc tcc ctg tct gca tcg gtg gga      48
Asp Ile Gln Met Thr Gln Ser Pro Ser Ser Leu Ser Ala Ser Val Gly
1               5                   10                  15 gac aga gtc act atc act tgc aag gcg agt cgg gac att aga agc tat      96
Asp Arg Val Thr Ile Thr Cys Lys Ala Ser Arg Asp Ile Arg Ser Tyr
            20                  25                  30 tta acc tgg tac cag cag aaa cca ggg aaa gct cct aag acc ctg atc     144
Leu Thr Trp Tyr Gln Gln Lys Pro Gly Lys Ala Pro Lys Thr Leu Ile
        35                  40                  45 tat tat gca aca agc ttg gca gat ggg gtc ccg tcg aga ttc agt ggc     192
Tyr Tyr Ala Thr Ser Leu Ala Asp Gly Val Pro Ser Arg Phe Ser Gly
    50                  55                  60 agt gga tct ggg caa gat tat tct ctc acc atc agc agc ctg gag tct     240
Ser Gly Ser Gly Gln Asp Tyr Ser Leu Thr Ile Ser Ser Leu Glu Ser
65                  70                  75                  80
```

```
gac gat aca gca act tac tac tgt cta caa cat ggt gag agt cca acg      288
Asp Asp Thr Ala Thr Tyr Tyr Cys Leu Gln His Gly Glu Ser Pro Thr
                85                  90                  95 ctc ggc tcg ggg acc aag ctg gaa atc aaa                              318
Leu Gly Ser Gly Thr Lys Leu Glu Ile Lys
            100                 105

<210> SEQ ID NO 5
<211> LENGTH: 109
<212> TYPE: PRT
<213> ORGANISM: Artificial Sequence
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala
            100                 105
```

MONOCLONAL ANTIBODY AND A METHOD THEREOF

CROSS REFERENCE TO RELATED APPLICATIONS

This application is a 35 USC §371 National Stage application of International Application No. PCT/IN2008/000562 filed Sep. 4, 2008, now pending; which claims the benefit under 35 USC §119(a) to India Patent Application No. 00650/CHE/2008 filed Mar. 14, 2008. The disclosure of each of the prior applications is considered part of and is incorporated by reference in the disclosure of this application.

FIELD OF THE INVENTION

The present invention relates to a humanized IgG1 isotype anti-CD6 antibody (T1h) that binds to the Scavenger receptor cysteine-rich (SRCR) domain 1 (D1) of CD6 present on the surface of thymic epithelial cells, monocytes, activated T cells and a variety of other cells types. The invention further relates to methods of inhibiting proliferation of T cells without blocking the interaction of CD6 and the natural CD6 ligands like Activated Leukocyte Cell Adhesion Molecule (ALCAM). It also relates to method of treatment of various disease indications using the anti-CD6 antibody that binds to the SRCR domain 1 (D1) of CD6.

BACKGROUND OF THE INVENTION

CD6 is an important cell surface protein predominantly expressed by human T cells and a subset of B cells, as well as by some B cell chronic lymphocytic leukemias and neurons [Aruffo et al., *J. Exp. Med.* 1991, 174:949; Kantoun et al., *J. Immunol.* 1981, 127:987; Mayer et al., *J. Neuroimmunol.* 1990. 29:193]. CD6 is a member of a large family of proteins characterized by having at least one domain homologous to the scavenger receptor cysteine-rich domain (SRCR) of type I macrophages [Matsumoto, et al., *J. Exp. Med.* 1991, 173:55 and Resnick et al., *Trends Biochem. Sci.* 1994, 19:5]. Other members of this family include CD5 [Jones et al., *Nature.* 1986, 323:346]; cyclophilin C [Friedman et al. 1993, *PNAS* 90:6815]; complement factor I, which binds activated complement proteins C3b and C4b [Goldberger, et al., *J. Biol. Chem.* 1987, 262:10065]; bovine WC-1 expressed by .tau./.delta. T cells [Wijingaard et al., *J. Immunol.* 1992, 149:3273] and M130 [Law et al., *Eur. J. Immunol.* 1993, 23:2320], a macrophage activation marker.

Blocking studies using anti-CD6 monoclonal antibodies (mAbs) suggest that CD6 plays an important role in T cell development by regulating T cell adhesive interactions with thymic epithelial (TE) cells [Patel et al., *J. Exp. Med.* 1995 181:1563-1568]. Additional studies have shown that CD6 can function as an important accessory molecule in T cell activation. For example, certain anti-CD6 mAb are directly mitogenic for T cells [Gangemi et al., *J. Immunol.* 1989, 143:2439 and Bott et al., 1993 *Int. Immunol.* 7:783], whereas others are able to co-stimulate T cell proliferation in conjunction with anti-CD3, anti-CD2 or phorbol 12 myristate 13 acetate (PMA) [Gangemi et al., *J. Immunol.* 1989, 143:2439; Morimoto et al., *J. Immunol.* 1988, 140:2165-2170; and Osorio et al., *Cell. Immunol.* 1994, 154:23]. Yet additional evidence of the role of CD6 in T cell activation comes from studies showing that CD6 becomes hyperphosphorylated on Ser and Thr residues [Swack et al., *Mol. Immunol.* 1989 26:1037-1049 and *J. Biol. Chem.* 1991, 266:7137; Cardenas et al., *J. Immunol.* 1990, 145:1450-1455] and phosphorylated on Tyr residues [Wee et al., *J. Exp. Med.* 1993, 177:219-223] following T cell activation. These and other studies implicate CD6 as an important modulator of both immature and mature T cell function in vivo, affecting both T cell activation and signal transduction.

The extracellular domain of the mature CD6 protein is composed of three SRCR domains (hereinafter designated D1, D2, and D3). D3 corresponding to the membrane proximal SRCR domain followed by a short 33-amino-acid stalk region. These extracellular domains are anchored to the cell membrane via a short transmembrane domain followed by a cytoplasmic domain of variable length [Aruffo et al., *J. Exp. Med.* 1991, 174:949].

Studies using CD6-immunoglobulin fusion proteins, containing selected extracellular domains of CD6 fused to human IgG$_1$ constant domains (CD6-Rgs), led to the identification and cloning of a CD6 ligand, designated "activated leukocyte cell adhesion molecule" (ALCAM) [Wee, et al., *Cell. Immunol.* 1994, 158:353-364; Patel, et al., *J. Exp. Med.* 1995. 181:1563-1568; Bowen et al., *J. Exp. Med.* 1995, 181:2213-2220]. ALCAM binds to domain 3 of CD6 corresponding to the membrane proximal SRCR domain [Whitney, et. al., *J. Biol. Chem.* 1995, 270: 18187-18190]

Studies of the role of CD6/ALCAM interactions in T cell regulation have shown that this receptor-ligand pair is able to mediate the adhesion of CD6 expressing cells to thymic epithelial cells [Bowen et al., *J. Exp. Med.* 1995, 181:2213]. This and other evidence suggests that CD6/ALCAM interactions are important for modulating T cell development and activation.

Although the functional characterization of CD6 remains incomplete, an anti-CD6 mAb have been successfully applied in a clinical setting to purge bone marrow of T cells and T cell precursors. The finding that patients receiving anti-CD6-treated allogeneic bone marrow had a low incidence of graft-vs-host disease coupled with high levels of engraftment [Soiffer R J, 1993, *Bone Marrow Transplant.*; 12 *Suppl* 3:S7-10] led to the discovery of a small subset of peripheral blood T cells (5-6%) that are CD6 negative (Rasmussen. *J Immunol* 1994. 152: 527-536). Subpopulation of CD6 negative T cells displayed lower alloreactivity in MLRs compared with normal CD6$^+$ T cells. (Rasmussen. *J Immunol* 1994. 152: 527-536). Functional characterization of these CD6-negative T cells has also shown that they are unresponsive to allostimulation, but can proliferate when stimulated with phytohemagglutin (PHA). These findings further support the hypothesis that CD6 plays an important role in modulating T cell function in vivo. CD6 is also reported to be part of the immunologic synapse mediating early and late T cell—APC interaction. (Gimferrer I. *J Immunol* 2004. 173: 2262-2270).

The CD6 molecule is N glycosylated with a protease sensitive site and possesses intrachain disulphide bonds. Previous reports indicated that CD6 exists in two molecular forms, a phosphorylated form of 105 kDa in resting T cells and a hyperphosphorylated form of 130 kDa in cells after protein kinase C activation by the tumor promoter, phorbol 12 myristate 13 acetate (PMA) (Osorio M, *Cellular Immunology,* 1994 154:123-133,).

U.S. Pat. No. 6,372,215 discloses antibodies and other binding agents that bind specifically to SRCR domains 3 (D3) of human CD6 (hCD6) or human CD6 stalk domain (CD6S) and inhibit activated leukocyte cell adhesion molecule (ALCAM) binding to CD6 the contents of which are herein incorporated by reference.

Cuban patent application CU 250/2006 dated 26 Dec. 2006 titled "Pharmaceutical composition comprising the anti CD6 monoclonal antibody useful for the diagnosis and treatment of Rheumatoid Arthritis" discloses that T1h binds to CD6 without inhibiting the binding of CD6 to the ALCAM ligand the contents of this application are herein incorporated by reference.

The CD6 antibody of the current invention prevents the activation of T cells by inhibiting T cell proliferation by binding to a domain independent to the domain interacting with the known ligand to CD6 namely ALCAM.

Earlier publications and patents discloses sequences of the murine anti-CD6 (IOR-T1) monoclonal and the amino acid modifications that were carried out to humanize IOR-T1 to T1h (humanized IOR-T1). U.S. Pat. No. 5,712,120 and its equivalent EP 0699755 disclose specific methods to humanize murine monoclonal antibodies and the sequence of IOR-T1 and T1h. U.S. Pat. No. 6,572,857 and its equivalent EP 0807125 disclose the sequence of IOR-T1 and T1h (humanized IOR-T1). The publication [Roque-Navarro, L., et. al., *Hybridoma and Hybridomics* 2003.22:245-257] discusses specific methods to humanize murine monoclonal antibodies and the sequence of IOR-T1 and T1h.

Aspects of the present invention relate to amino acid sequences of the variable region of heavy and light chain of T1h. This establishes the T1h nucleotide and amino acid sequence as expressed by the cell line used for manufacturing T1h. The monoclonal antibody of the present invention is capable of binding to domain 1 (D1) of CD6 and inhibits T-cell proliferation without interfering with ALCAM binding. The monoclonal antibody of the present invention does not induce complement dependent cytotoxicity (CDC), antibody dependent cytotoxicity (ADCC) and apoptosis in vitro.

OBJECTIVE OF THE INVENTION

The main objective of the present invention is to obtain a monoclonal antibody capable of binding to domain 1 (D1) of CD6 and inhibits T cell proliferation without interfering with ALCAM binding.

Another main objective of the present invention is to obtain method for modulating inflammatory conditions using the monoclonal antibody.

Yet another main objective of the present invention is to obtain a method for modulating inflammatory conditions using the monoclonal antibody in combination with immunosuppressants.

Still another main objective of the present invention is to obtain a method for modulating inflammatory conditions using the monoclonal antibody in combination with antigens capable of eliciting an anti-inflammatory immune response like Insulin, GAD, MOG, MBP and HSP60.

STATEMENT OF THE INVENTION

Accordingly, the present invention relates to a monoclonal antibody capable of binding to domain 1 (D1) of CD6 and inhibits T cell proliferation without interfering with ALCAM binding; a method for modulating inflammatory conditions like psoriasis, rheumatoid arthritis or autoimmune responses in patients like adverse responses associated with multiple sclerosis or transplant rejection, graft-versus-host disease, type-1 diabetes, psoriasis, cutaneous T cell lymphoma, thyroditis and other T cell mediated autoimmune diseases using the monoclonal antibody; a method for modulating inflammatory conditions like psoriasis, rheumatoid arthritis or autoimmune responses in patients like adverse responses associated with multiple sclerosis or transplant rejection, graft-versus-host disease, type-1 diabetes, psoriasis, cutaneous T cell lymphoma, thyroditis and other T cell mediated autoimmune diseases using the monoclonal antibody in combination with immunosuppressants; and a method for modulating inflammatory conditions like multiple sclerosis or transplant rejection, graft-versus-host disease, type-1 diabetes, using the monoclonal antibody in combination with antigens capable of eliciting an anti-inflammatory immune response like Insulin, GAD, MOG, MBP and HSP60.

BRIEF DESCRIPTION OF ACCOMPANYING FIGURES

FIG. 1a: Nucleotide sequence of VH (SEQ ID NO: 3) and Vk (SEQ ID NO: 4) of T1h derived from plasmid and genomic DNA.

FIG. 1b: Amino acid sequence of VH (SEQ ID NO: 1) and Vk (SEQ ID NO: 2).

FIG. 1c: Comparison of Vk amino acid sequence (SEQ ID NO: 5) disclosed in previous publications (EP0807125B1) as compared to the sequence (SEQ ID NO: 2) disclosed in this patent to highlight the sequence differences.

FIG. 2: ELISA reading of plate tethered with CD6-Fc in the presence of T1h and ALCAM or T1h alone.

Figure 3:
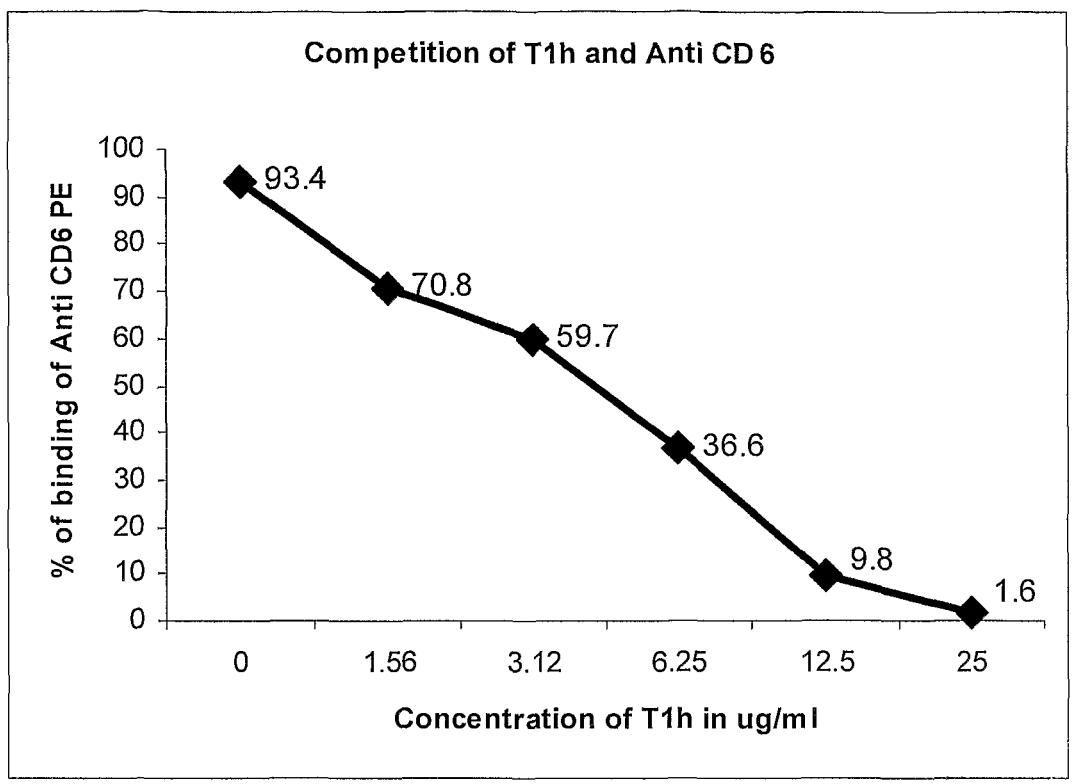

FIG. 3: When MEM 98, an antibody which binds to domain 1 (Castro A A M et al, *J of Immunol,* 178 (2007) 4351-4361.), is competed with T1h there is a dose dependent competition observed, suggesting that both bind to the same domain namely Domain 1.

Figure 4:
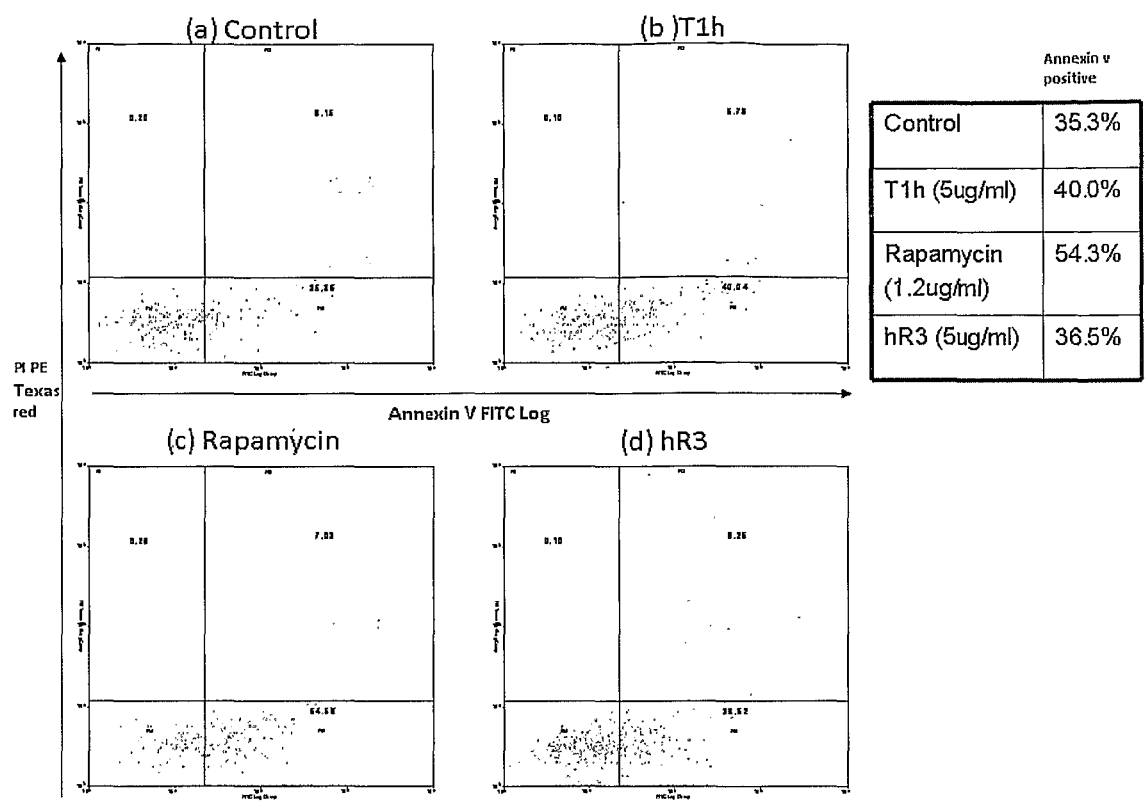

FIG. 4: HUT 78 cells treated with T1h antibody (5 ug/ml), hR3 antibody (5 ug/ml), and rapamycin (1.2 ug/ml) or without antibody (as control) and incubated overnight at 37° C. in a $CO_2$ incubator. Cells were then treated with Annexin V labeling solution followed by flow cytometry analysis. Annexin V FITC log on horizontal axis, PI/PE texas red on vertical axis.

Figure 5:
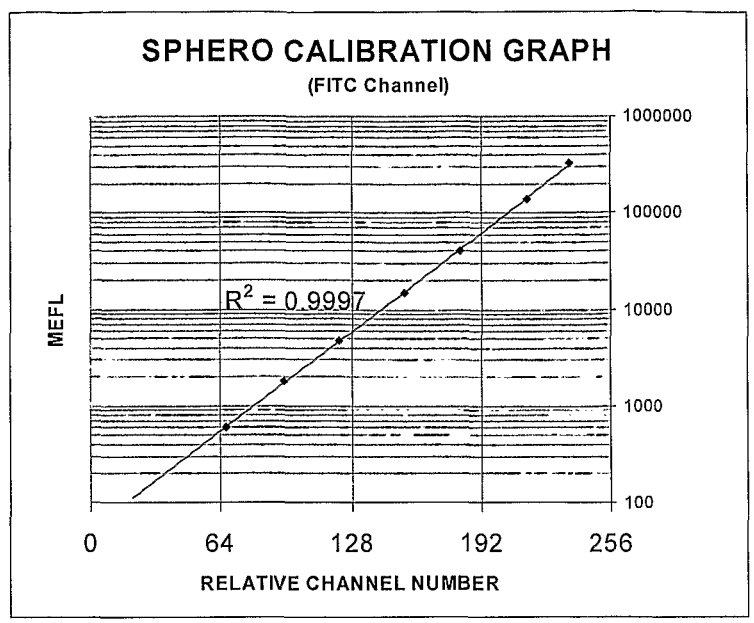

FIG. 5: Sphero calibration Graph for the FITC channel.

Figure 6:
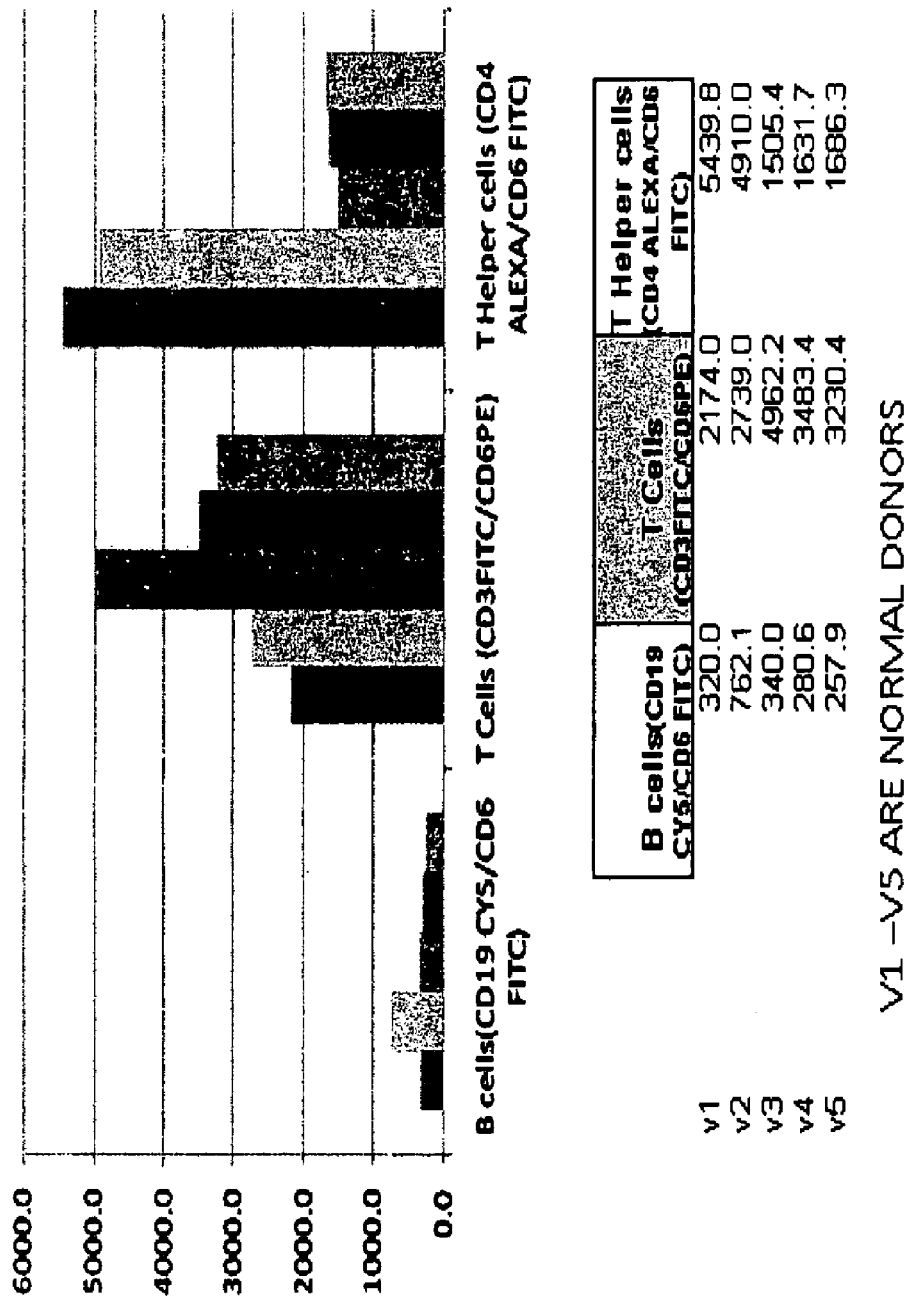

FIG. 6: Density of CD6 receptors on the T and B lymphocytes of the various healthy individuals. T cells show 10 times more CD6 receptors than B cells positive for CD6

Figure 7:
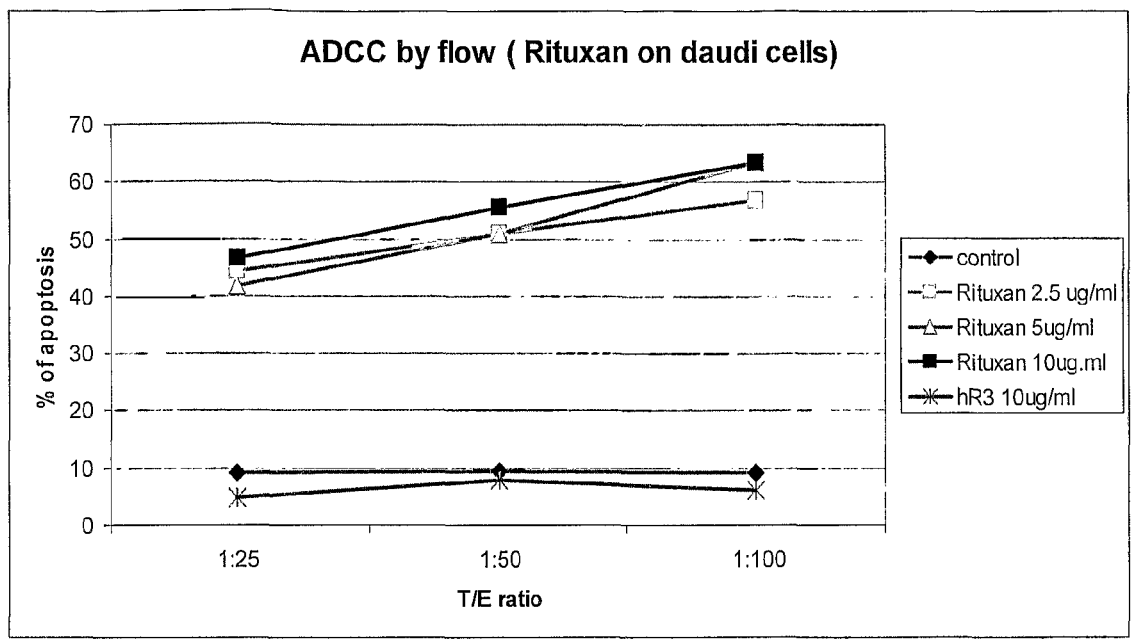

FIG. 7: ADCC assay was analyzed using Rituxan as a positive control on Daudi cells. Daudi cells was labeled with CFSE and incubated with or without Rituxan (2.5, 5 & 10 ug/ml), hR3 (10 ug/ml) used as non specific control and PBMCs were used as Effector cells at ratio of 1:25, 1:50, 1:100. The cells were incubated for 6 hours. 7AAD was used to detect the cytotoxic cells. Cells were analyzed in CYAN ADP flow cytometry.

Figure 8:
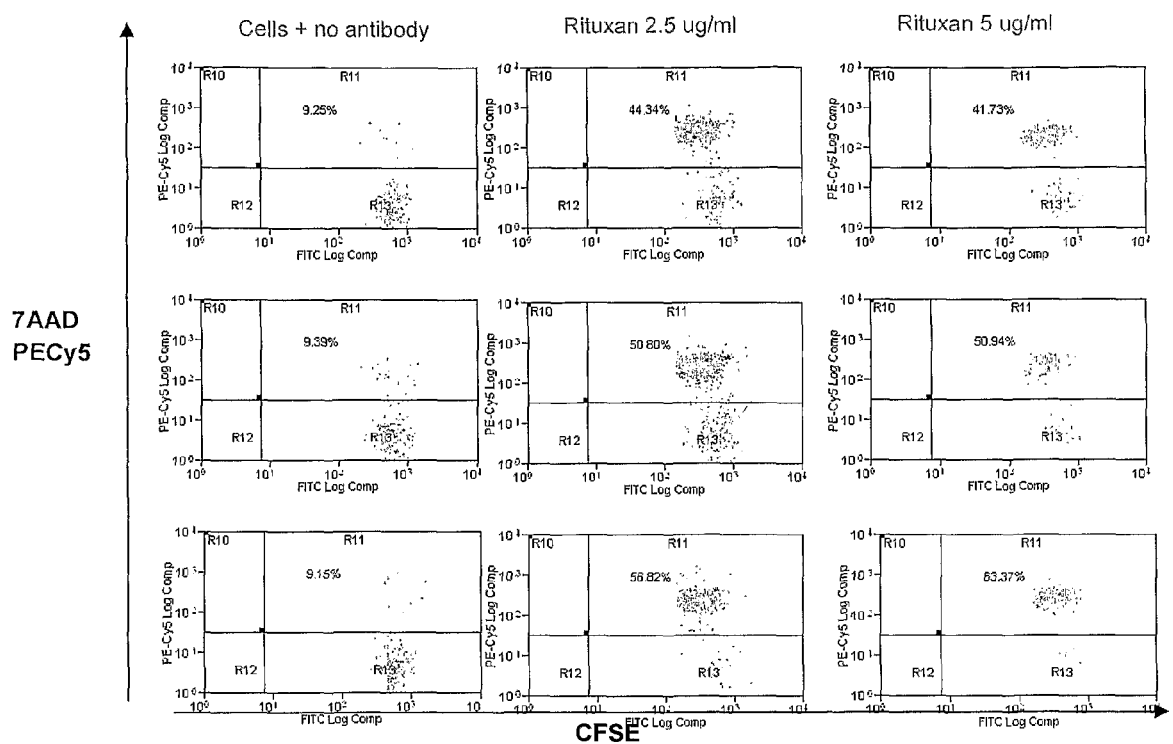

FIG. 8: ADCC assay on Daudi cells by Rituxan in 2 D dotplot

Figure 9:
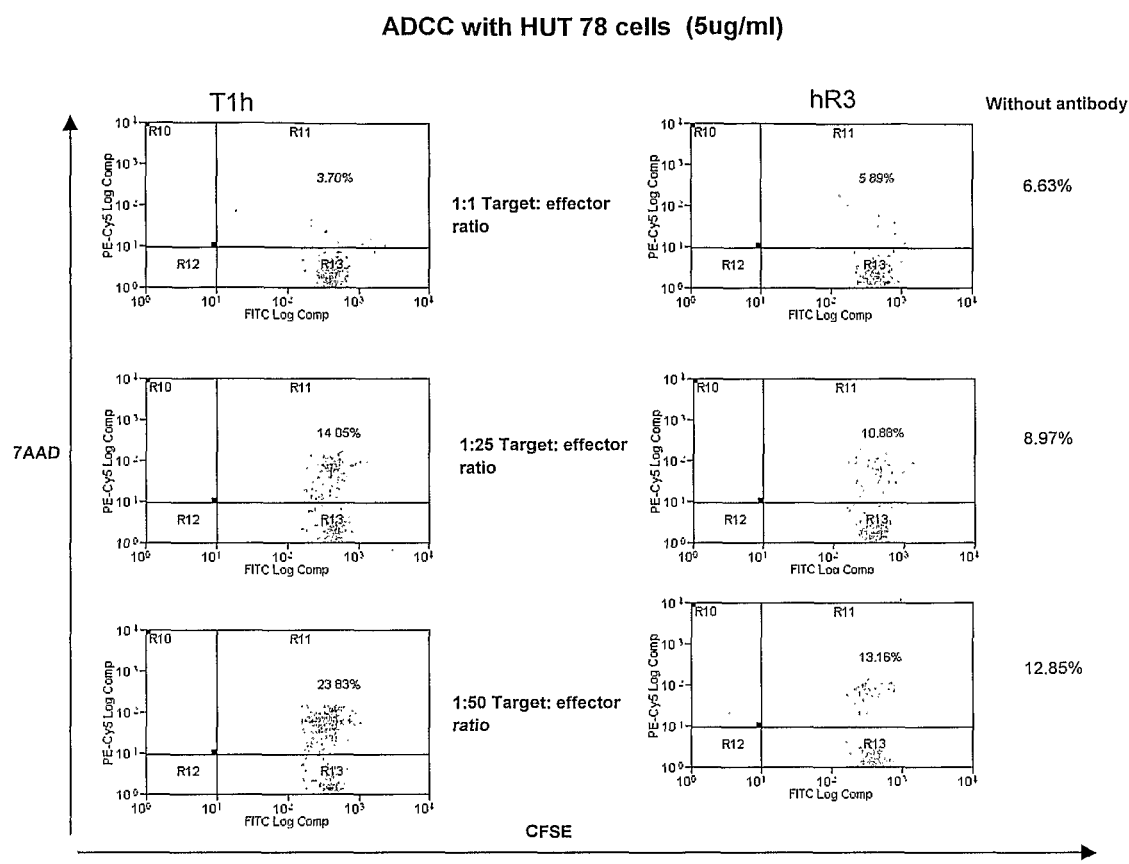

FIG. 9: ADCC assay on HUT 78 in 2 D dotplot with 5 µg/ml of T1h

Figure 10:
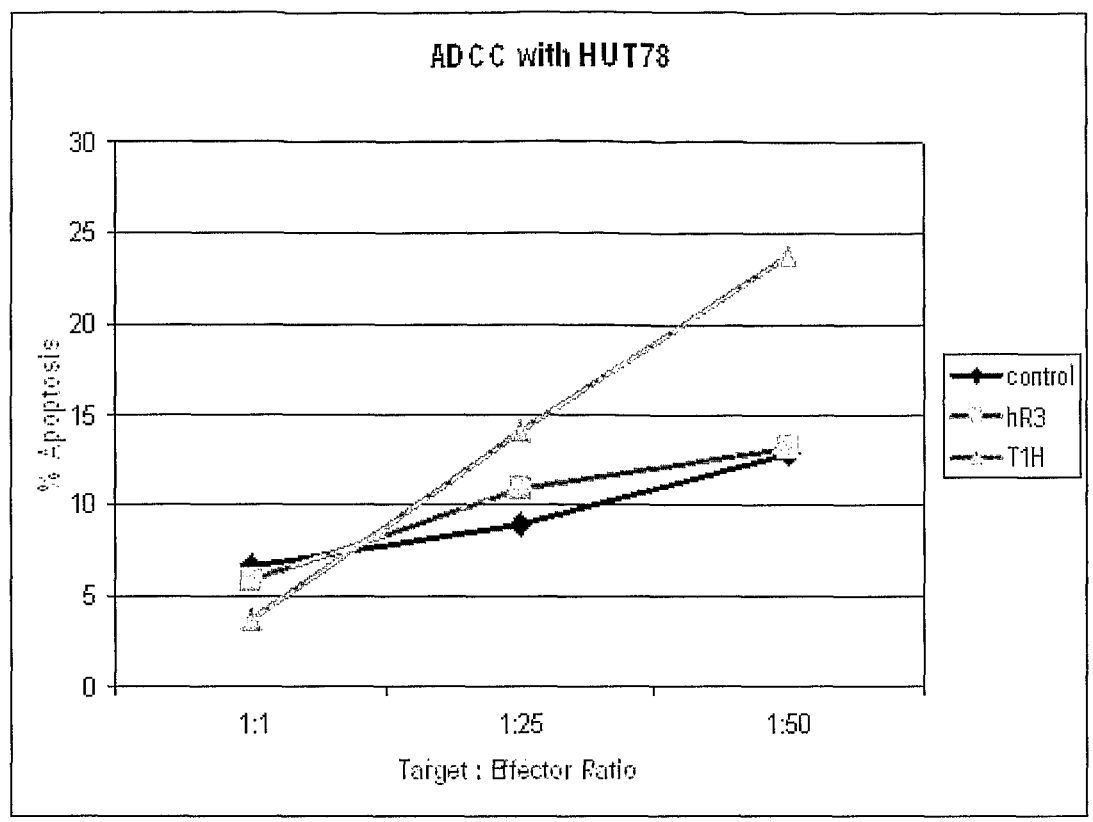

FIG. 10: The role of T1h in ADCC assay. HUT 78 was labeled with CFSE and incubated with and without T1h antibody, hR3 is used as non specific control and PBMCs were used as Effector cells at ratio of 1:1, 1:25, 1:50. The target: Effector cells were incubated overnight. 7AAD was used to detect the cytotoxic cells. Cells were analyzed by flow cytometry FIG. 11: The role of T1h in ADCC assay. HUT 78 was labeled with CFSE and incubated with and without T1h antibody (5 & 10 ug/ml), hR3 (10 ug/ml) used as non specific control and PBMCs were used as Effector cells at ratio of 1:1, 1:25, 1:50. The target:Effector cells were incubated overnight. 7AAD was used to detect the cytotoxic cells. Cells were analyzed by flow cytometry FIG. 12: a,b and c,d represent two independent experiments at 5 µg/ml and 10 µg/ml respectively of T1h and hR3

(Non specific antibody) respectively. Graphs represent percentage of dead cells at different target:effector ratios.

Figure 13:
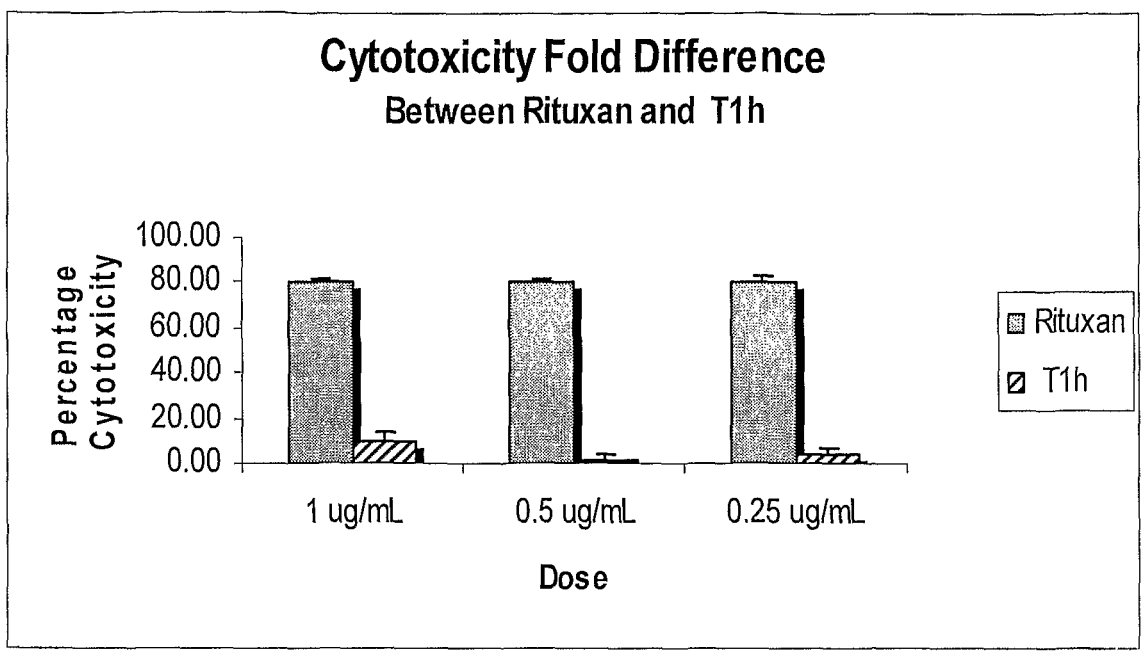

FIG. 13: Cytotoxicity fold difference between Rituxan and T1h in CDC assay using Alamar Blue.

Figure 14:
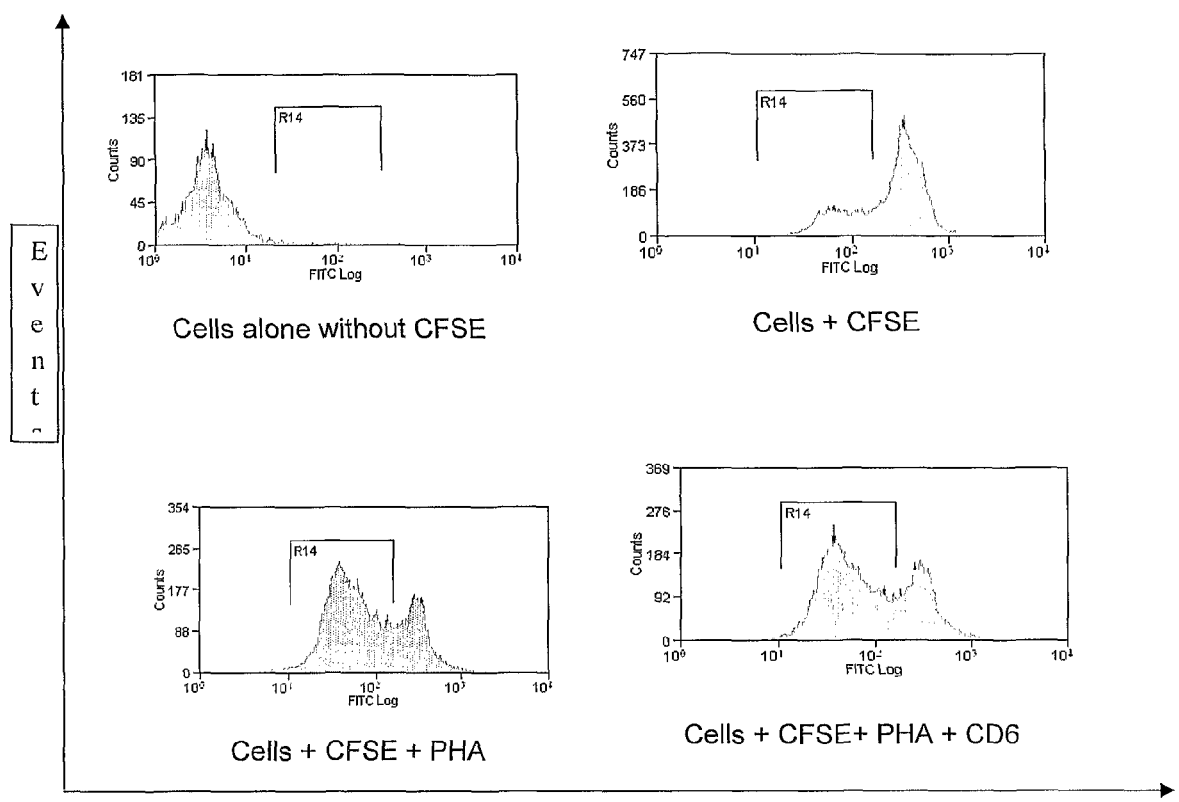

FIG. 14: Histogram plot of CFSE showing the fluorescence intensity of unstimulated and phytohemagglutin (PHA-M) stimulated cells. FITC log on horizontal axis, no of cells on the vertical axis. Region (R 14) above the peaks were used to enumerate events as proliferation.

Figure 15:
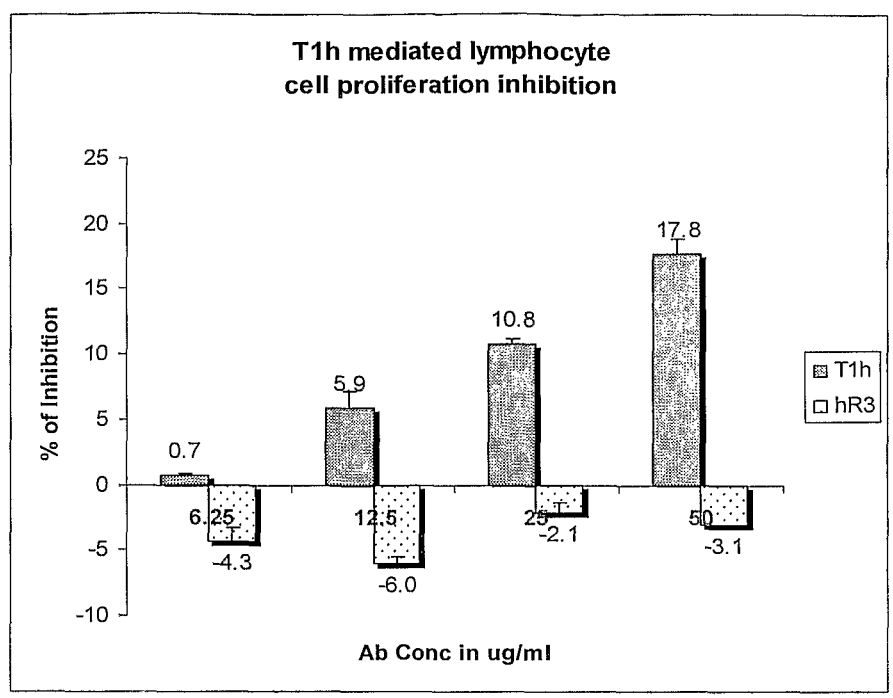

FIG. 15: Dose dependent inhibition of T1h on lymphocytes as bar graph. The figure represents the % of inhibition of T1h on PHA activate lymphocytes at various concentration (50 ug/ml, 25 ug/ml, 12.5 ug/ml, 6.25 ug/ml). hR3 (non specific antibody) was used at the same concentration.

Figure 16:
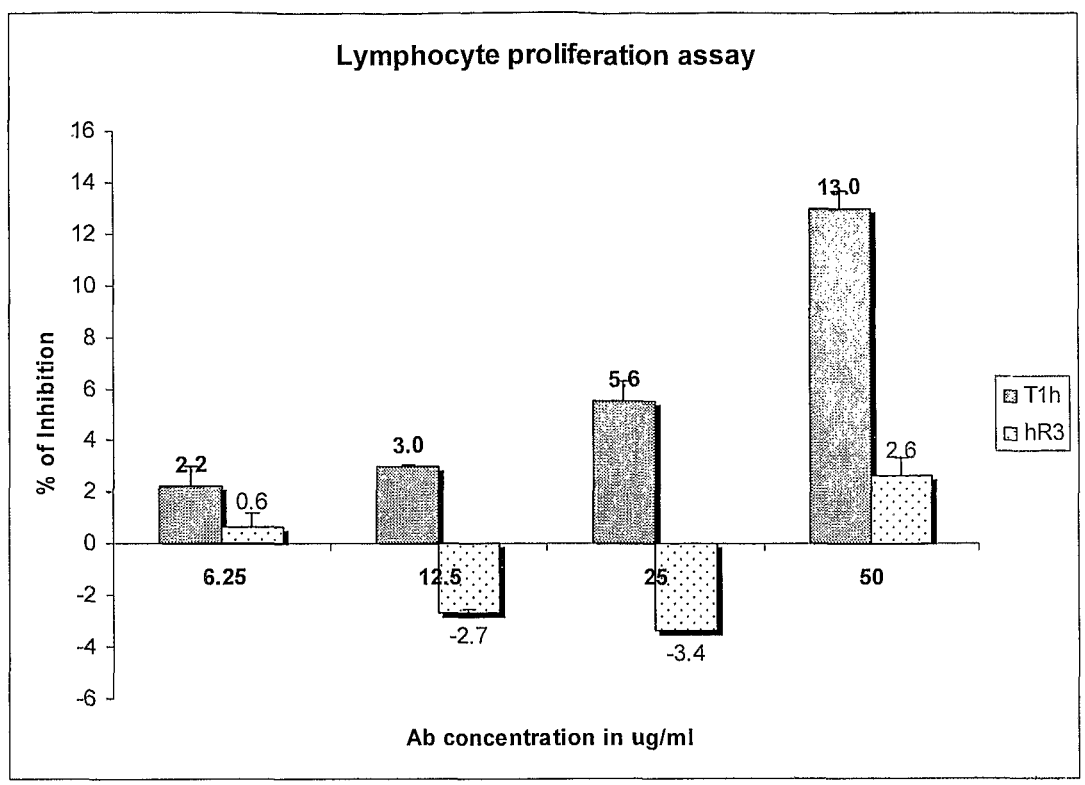

FIG. 16: Repeat of previous experiment as an independent experiment. Dose dependent inhibition of T1h on lymphocytes. The figure represents the % of inhibition of T1h on PHA activate lymphocytes at various concentration (50 ug/ml, 25 ug/ml, 12.5 ug/ml and 6.25 ug/ml). hR3 (non specific antibody) was used at the same concentration FIG. 17: Presence of soluble T1h, at a concentration of 10 μg/ml, significantly inhibited PHA mediated proliferation of lymphocytes in 96 well plate based ALAMAR BLUE assay.

FIG. 18: Plate set up for the tethered experiments of Anti CD3, AntiCD3+ T1h and Anti CD3+ALCAM-Fc.

Figure 19:
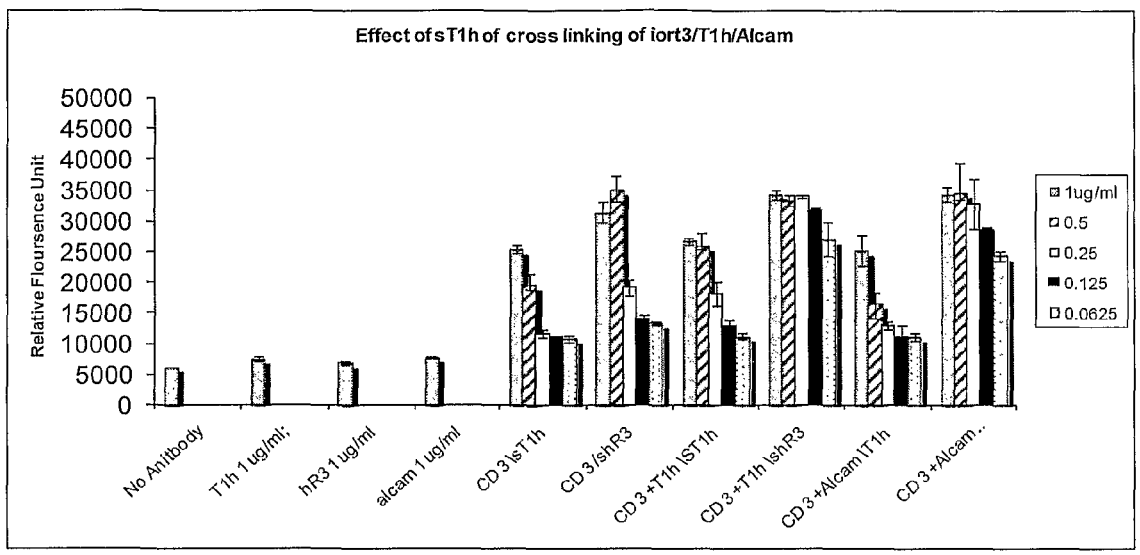

FIG. 19: Comparison between effects on lymphocyte proliferation by sT1h and shR3 (10 μg/ml) respectively in presence of tethered anti CD3, Anti CD3+T1h and Anti CD3+ ALCAM-Fc. As is mentioned in the protocol varying amounts of tethered Anti CD3 with fixed concentration of T1h or ALCAM were used.

Figure 20:
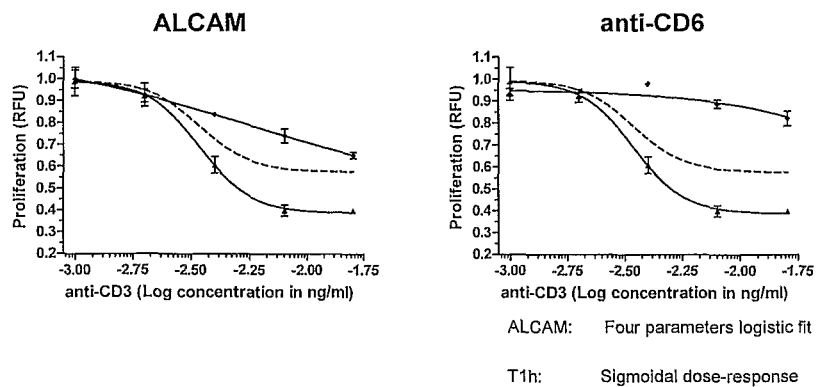

FIG. 20: Analysis of the previous data in BLISS where the lower line is the experimental curve obtained with varying concentration of Anti CD3 antibody and ALCAM-Fc or Anti CD6 antibody respectively. The dotted line is the predicted curve if the combination is additive. The upper line is the curve obtained experimentally and in both cases lies above the theoretical predicted curve suggesting that the combination is synergistic.

Figure 21:
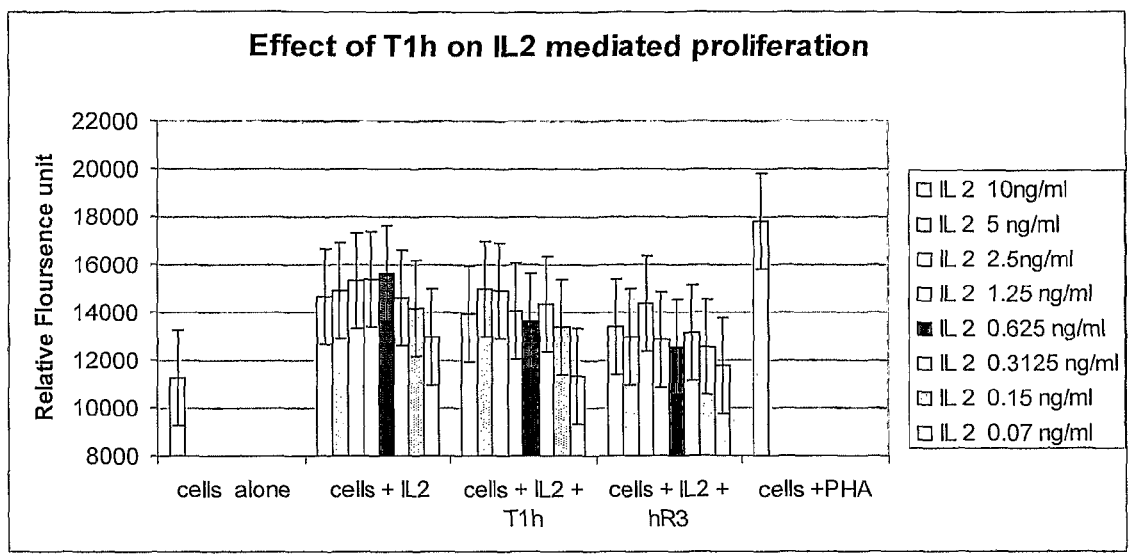

FIG. 21: Proliferation of Naïve T cells induced by IL2 at varying concentrations. Soluble T1h and soluble hR3 did not show any effect. PHA is added as a positive control.

Figure 22:
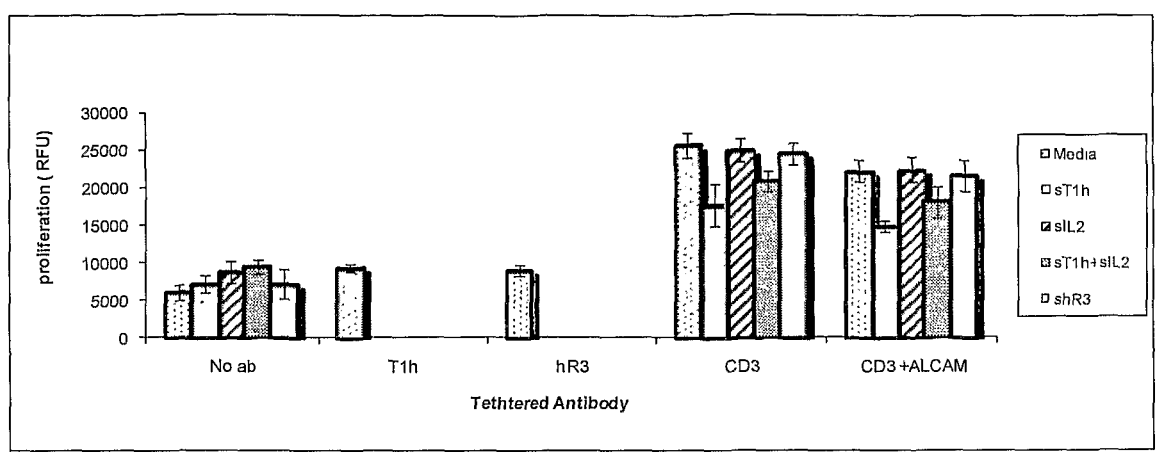

FIG. 22: Tethered CD3 and CD3+ALCAM-Fc caused lymphocyte proliferation which was inhibited by soluble T1h. IL2 along with soluble T1h showed partial recovery of the inhibition in both the conditions.

Figure 23:
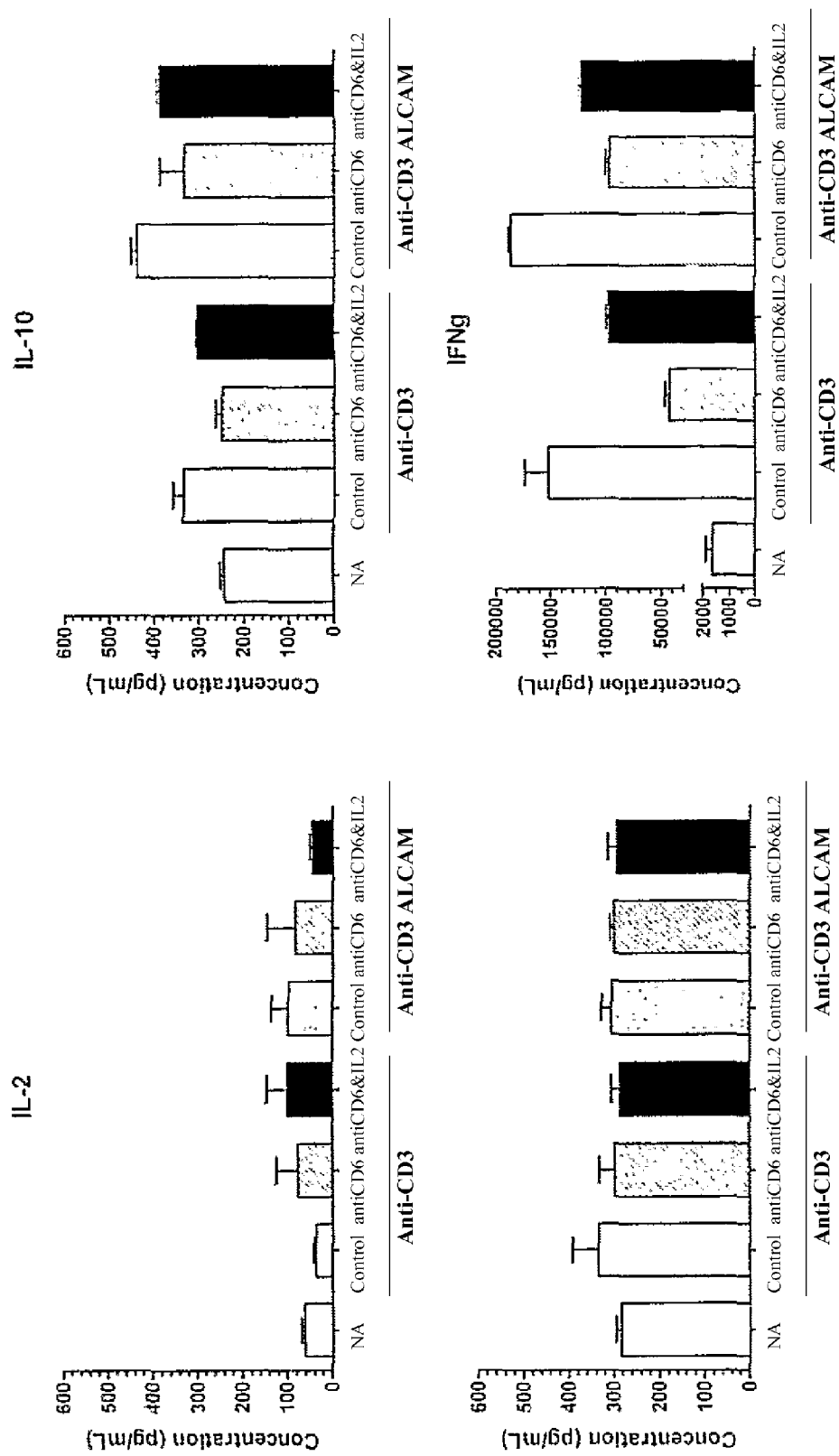
Figure 23:
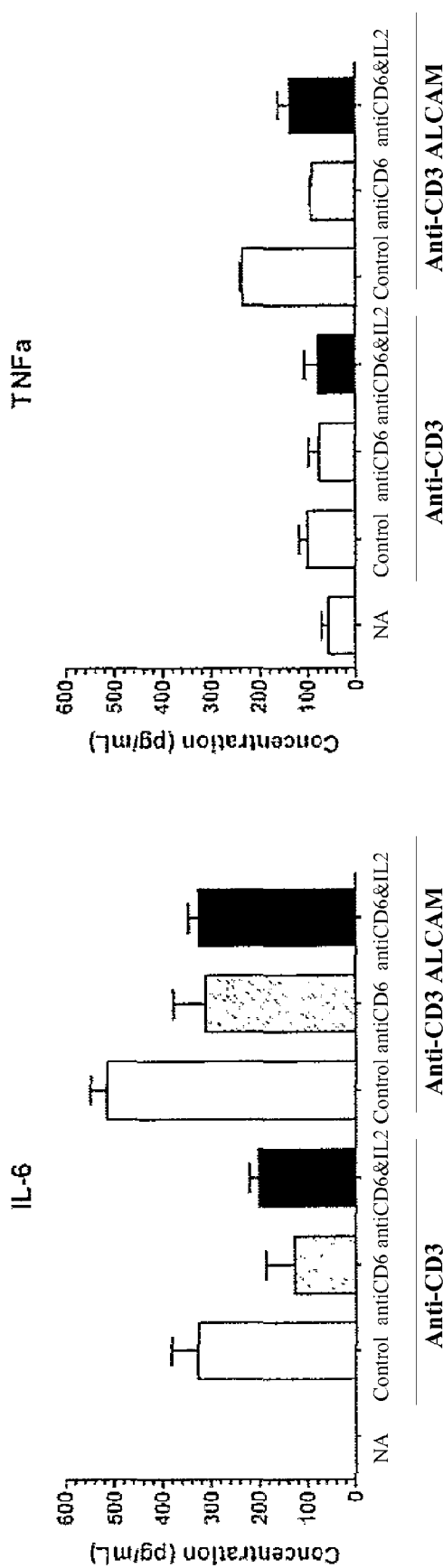

FIG. 23: IL10, INFγ, IL6 and TNF☐ expression is reduced by soluble T1h as compared to a control (soluble hR3 non specific antibody) in both the Anti CD3 and anti CD3+AL-CAM tethered wells. Exogenous IL2 added along with soluble T1h shows partial recovery of the inhibition, suggesting that inhibition of soluble T1h is mediated by downregulation of IL2. Experiment shows mean of data from two independent experiments.

Figure 24:
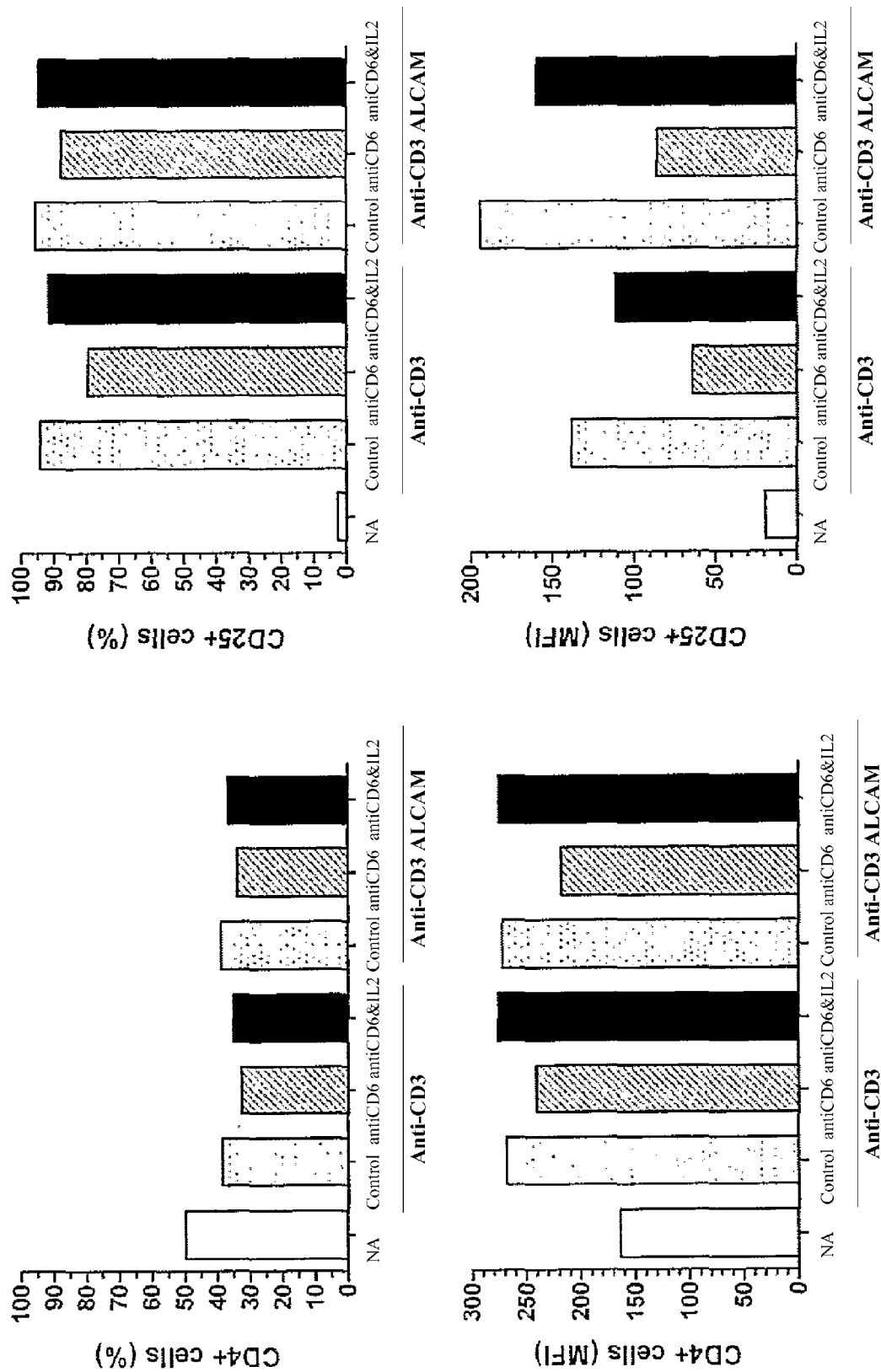

FIG. 24: There is partial reduction of absolute cell counts expressing CD4 and CD25 in presence of soluble T1h (sT1h) which is recovered upon addition of both sT1h and exogenous IL2. However in the mean fluorescent intensity which can be correlated to absolute receptor counts, there is significant reduction of MFI in CD4 and more spectacularly in the CD25 counts. Both these reductions can be fully or partially recovered respectively by addition of exogenous IL2 (1.2 ng/ml). This phenomenon is observed in both the tethered Anti CD3 and tethered Anti CD3 and ALCAM-Fc wells.

Figure 25:
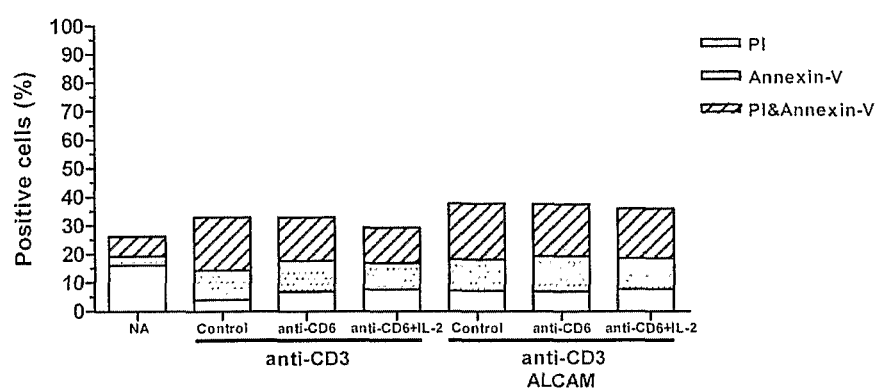

FIG. 25: Inhibition of proliferation by soluble T1h is not mediated by increased apoptosis. PI positive cells are necrotic cells while Annexin V FITC positive cells are apoptotic cells and both positive are late apoptotic cells. From the data it is clear that as compared to the control there is no significant increase or decrease in each of the death parameters across different combinations.

Figure 26:
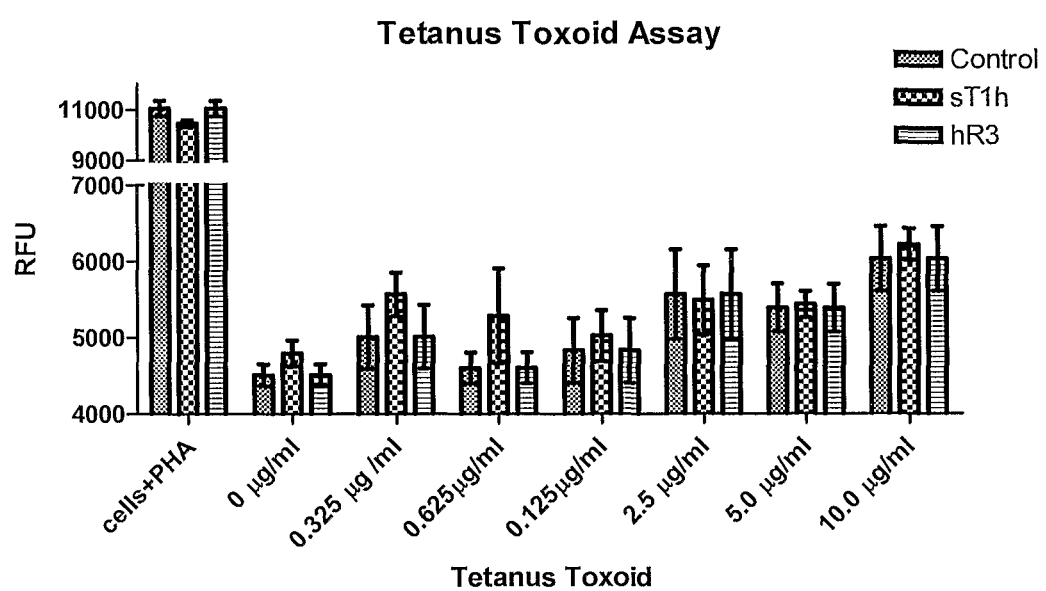

FIG. 26: PBMCs were treated with T1h antibody (10 ug/ml), hR3 (isotype control) or without antibody (as control) and incubated for 5 days at 37° C. in a $CO_2$ incubator. Cells were stimulated with the Tetanus toxoid before incubation. The proliferation was measured with Alamar blue dye. No inhibition of proliferation was observed in the presence of T1h.

Figure 27:
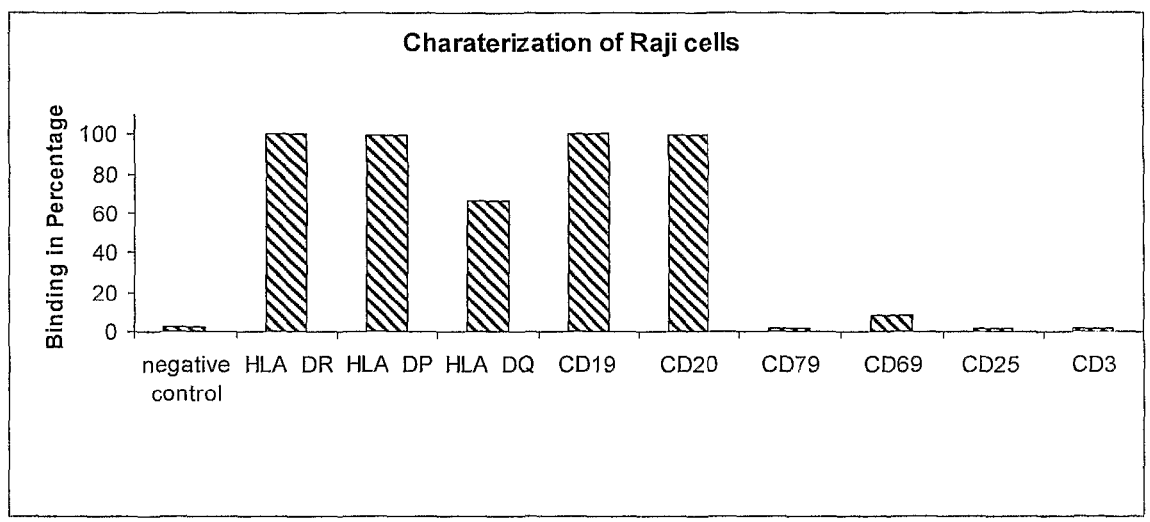

FIG. 27: Raji cells are shown here by immunofluorescence as mentioned before (Procedure II) to be true B cells and also express MHC II antigens.

Figure 28:
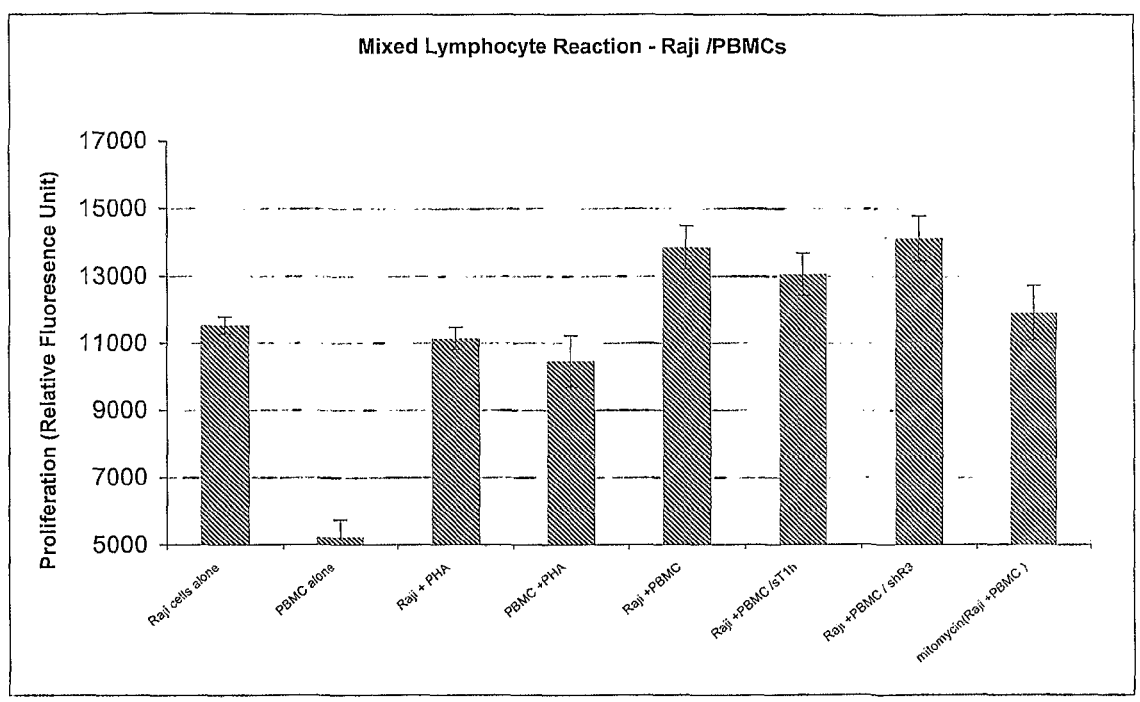

FIG. 28: PBMCs proliferative in presence of mitomycin treated Raji cells. Positive control shows that PBMCs grow in presence of PHA. sT1h inhibits T cell proliferation (significantly by t test) as compared to no antibody or hR3 controls. Each experiment is a mean and standard deviation obtained from six different wells.

FIG. 29: —Allogeneic Dendritic Cell Mixed Lymphocyte Reaction—Plate Setup.

Figure 30:
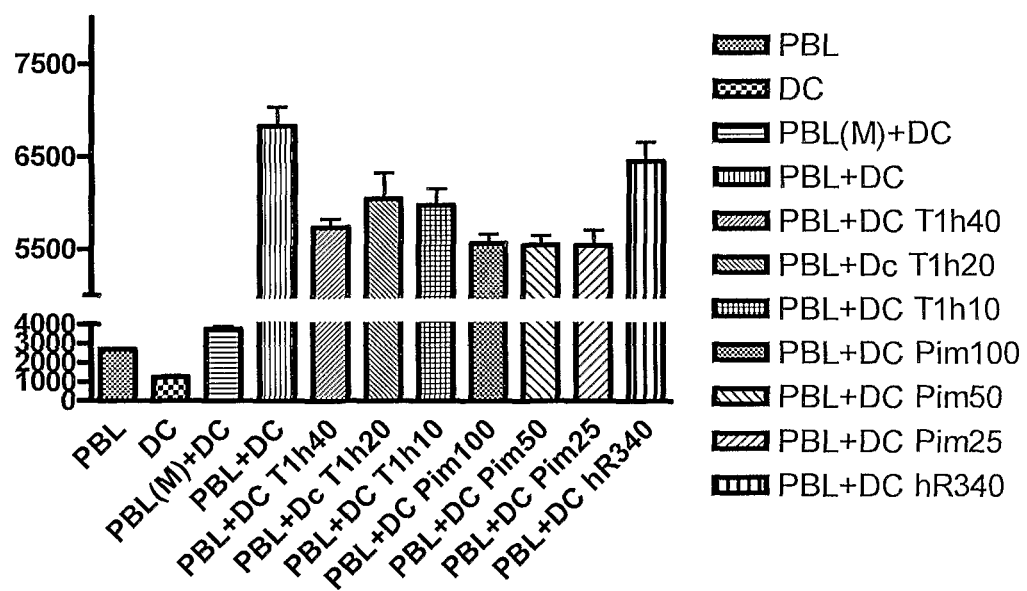

FIG. 30: Allogeneic Dendritic Cell Mixed Lymphocyte Reaction T1h shows dose dependent inhibition of PBMC Proliferation. Positive control Pimecrolimus which is a known inhibitor of IL2 inhibited at all the concentrations tested. Negative control hR3 was similar to the experimental control. Y axis is Relative Fluorescence Units (RFU).

Figure 31:
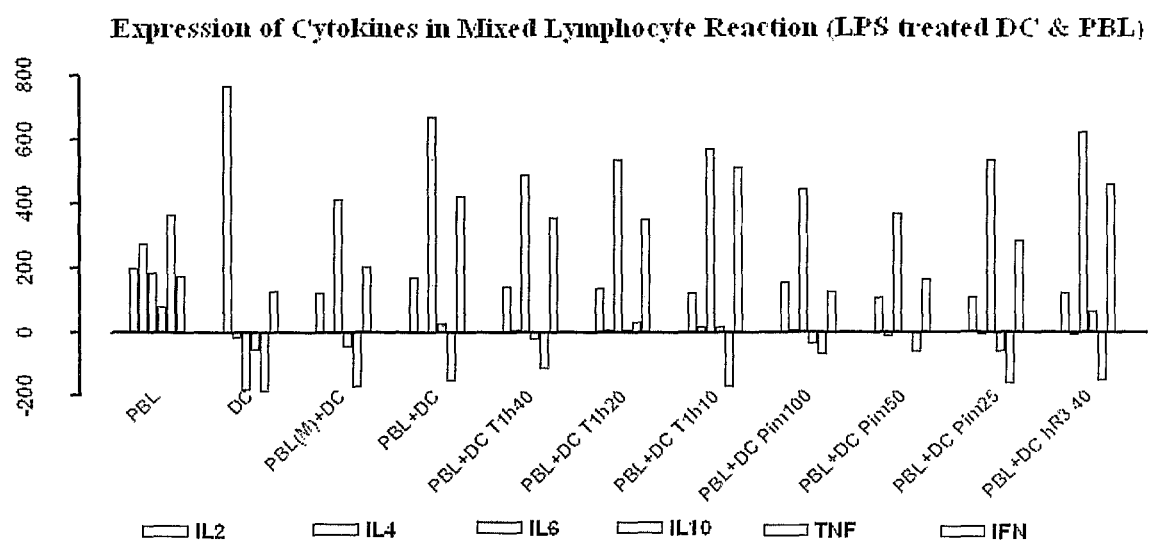

FIG. 31: Allogeneic Dendritic Cell Mixed Lymphocyte Reaction. Evaluation of Cytokine Levels. IL6 and INF γ are inhibited in a dose dependent manner by T1h as well as Pimecrolimus, a known IL2 inhibitor.

BRIEF DESCRIPTION OF ACCOMPANYING SEQUENCE LISTINGS

SEQ ID NO: 1: Amino acid sequence of VH sequence
SEQ ID NO: 2: Amino acid sequence of VK sequence
SEQ ID NO: 3: Nucleotide (DNA) sequence of VH sequence
SEQ ID NO: 4: Nucleotide (DNA) sequence of VK sequence

DETAILED DESCRIPTION OF THE INVENTION

The present invention relates to a monoclonal antibody capable of binding to domain 1(D1) of CD6 and inhibits T cell proliferation without interfering with ALCAM binding.

In another embodiment of the present invention, the monoclonal antibody comprising an amino acid sequence which is at least 80% homologous to the amino acid sequence as set forth in SEQ ID NO: 1 or SEQ ID NO: 2.

In yet another embodiment of the present invention, the monoclonal antibody comprising an amino acid sequence which is at least 80% homologous to the nucleotide sequence as set forth in SEQ ID NO: 3 or SEQ ID NO: 4.

In still another embodiment of the present invention, the antibody does not induce complement dependent cytotoxicity (CDC) in vitro In still another embodiment of the present invention, the antibody does not induce antibody dependent cytotoxicity (ADCC) in vitro In still another embodiment of the present invention, the antibody does not induce apoptosis in vitro In still another embodiment of the present invention, the antibody inhibits the proliferation of naïve PBMCs induced by tethered anti-CD3; combination of tethered anti-CD3 and anti-CD6 or combination of tethered anti CD3 and ALCAM.

In still another embodiment of the present invention, the antibody specifically inhibits one way MLR where Raji cells are the Antigen Presenting Cells and PBMCs proliferate.

In still another embodiment of the present invention, the antibody specifically inhibits one way autologous MLR mediated by PBMCs.

In still another embodiment of the present invention, the antibody causes inhibition of naïve T cell proliferation by substantially decreasing the pro inflammatory cytokines.

In still another embodiment of the present invention, the antibody causes inhibition of naïve T cell proliferation by reduction in CD25 and CD4 counts.

In still another embodiment of the present invention, the antibody inhibits T cell proliferation by mediating suppression of IL2.

In still another embodiment of the present invention, the antibody shows gain of function with the addition of exogenous IL2.

In still another embodiment of the present invention, the antibody is involved in the down regulation of pro-inflammatory cytokines IL6 and INFγ.

In still another embodiment of the present invention, the antibody does not inhibit memory-T-cell population.

The present invention relates to a method for modulating inflammatory conditions like psoriasis, rheumatoid arthritis or autoimmune responses in patients like adverse responses associated with multiple sclerosis or transplant rejection, graft-versus-host disease, type-1 diabetes, psoriasis, cutaneous T cell lymphoma, thyroditis and other T cell mediated autoimmune diseases using the monoclonal antibody according to one or more of the preceding claims.

The present invention relates to a A method for modulating inflammatory conditions like psoriasis, rheumatoid arthritis or autoimmune responses in patients like adverse responses associated with multiple sclerosis or transplant rejection, graft-versus-host disease, type-1 diabetes, psoriasis, cutaneous T cell lymphoma, thyroditis and other T cell mediated autoimmune diseases using the monoclonal antibody in combination with immunosuppressants.

The present invention relates to a method for modulating inflammatory conditions like multiple sclerosis or transplant rejection, graft-versus-host disease, type-1 diabetes, using the monoclonal antibody in combination with antigens capable of eliciting an anti-inflammatory immune response like Insulin, GAD, MOG, MBP and HSP60.

In another embodiment of the present invention, the method includes administration to a patient of a therapeutically or pharmaceutically effective amount of an anti-CD6 binding antibody that binds specifically to human CD6 SRCR domain 1 (D1) and does not inhibit ALCAM binding to hCD6.

In yet another embodiment of the present invention, the pharmaceutically effective dose is 0.1-25 mg/kg/week.

In still another embodiment of the present invention, the monoclonal antibody is represented by an amino acid sequence which is at least 80% homologous to the amino acid sequence as set forth in SEQ ID NO: 1 or SEQ ID NO: 2.

In another embodiment of the present invention, the monoclonal antibody is represented by an nucleotide sequence which is at least 80% homologous to the amino acid sequence as set forth in SEQ ID NO: 3 or SEQ ID NO: 4.

Reference will now be made in detail to the presently preferred embodiments of the invention which, together with the following examples, will serve to explain the principles of the invention.

The Examples which follow are set forth to aid in understanding the invention but are not intended to, and should not be construed to limit its scope in any way. The Examples do not include detailed descriptions for conventional methods employed in the assay procedures. Such methods are well known to those of ordinary skill in the art and are described in numerous publications including by way of examples.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

In describing and claiming the present invention, the following terminology will be used in accordance with the definitions set out herein.

"Anti-CD6 antibody" is an antibody that bind specifically to SRCR domain 1 (D1) of human CD6 (hCD6). In preferred aspects of the invention, antibodies and other immunoglobulins, including native and artificially modified antibodies and antibody fragments, are provided that bind specifically to human SRCR domain 1 of CD6 and that do not interfere with the activated leukocyte cell adhesion molecule (ALCAM) binding to CD6.

The T1h monoclonal antibody of the present invention also encompasses an antibody comprising a heavy chain and/or light chain having an amino acid sequence derived from the amino acid sequence of a heavy chain or light chain constituting an antibody by deletion, substitution, or addition of one or several amino acids. The above-mentioned partial amino acid modification (deletion, substitution, insertion, or addition) can be imparted to the amino acid sequence of the antibody of the present invention by partially modifying the nucleotide sequence encoding the amino acid sequence. Such partial modification of a nucleotide sequence can be imparted by a standard method using known forms of site-specific mutagenesis (*Prot Natl Acad Sci U.S.A.*, 1984 Vol 81: 5662).

One preferred embodiment of the invention represents a monoclonal antibody which specifically binds to Scavenger receptor cysteine-rich (SRCR) domain 1 (D1) of CD6 comprises heavy chain and light chain variable region comprising an amino acid sequence which is at least 80% homologous to the amino acid sequence as set forth in SEQ ID NO: 1 and SEQ ID NO: 2.

Another preferred embodiment of the invention represents a monoclonal antibody which specifically binds to Scavenger receptor cysteine-rich (SRCR) domain 1 (D1) of CD6 which comprises heavy chain and light chain variable region comprising the nucleotide sequence set forth in SEQ ID NO: 3 or a complement thereof; and (b) a nucleic acid molecule comprising the nucleotide sequence set forth in SEQ ID NO: 4 or a complement thereof.

According to an embodiment, the anti-CD6 antibody variant T1h of the present invention which specifically binds to Scavenger receptor cysteine-rich (SRCR) domain 1(D1) of CD6 will have at least about 65% amino acid sequence identity or homology, at least about 70% amino acid sequence identity or homology, at least about 75% amino acid sequence identity or homology, at least about 80% amino acid sequence identity or homology, at least about 80% amino acid sequence identity or homology, at least about 85% amino acid sequence identity or homology, at least about 90% amino acid sequence identity or homology, at least about 95% amino acid sequence identity or homology, at least about 98% amino acid sequence identity or at least about 99% amino acid sequence identity or homology in that portion corresponding to amino acid residues represented by the SEQ ID Nos 1 & 2.

The antibody of the present invention does not induce complement-dependent cytotoxicity (CDC) in-vitro.

The antibody of the present invention does not induce antibody dependent cytotoxicity (ADCC) in-vitro.

The antibody of the present invention does not induce apoptosis in-vitro.

In another aspect, the present invention further provides a preventive, therapeutic, or diagnostic agent for diverse diseases including auto-immune disorders, which contains the subject antibody of the present invention or a functional fragment thereof as an active ingredient.

Antibody dependent cytotoxicity (ADCC) refers to a type of cytotoxicity induced by activation of macrophages, NK cells, neutrophil cells, or the like that are recognized through the binding of antibody constant regions to Fc receptors expressed on the surfaces of the above cells. In contrast, complement dependent cytotoxicity (CDC) refers to a type of cytotoxicity induced by activation of a complement system that occurs through binding of an antibody to an antigen. It is known that the intensity of these activities vary depending on antibody subclasses. It is also known that such differences are due to structural differences among antibody constant regions (Charles A. Janeway et al., *Immunobiology*, 1997, Current Biology Ltd/Garland Publishing Inc.).

In other embodiments of the invention, the nucleotide and amino acid sequences of the variable region of heavy and light chain of T1h are disclosed. This establishes the T1h nucleotide and amino acid sequence as expressed by the cell line used for manufacturing T1h.

Screening methods are provided for identifying additional binding agents that specifically bind hCD6. These methods entail contacting a reference anti-hCD6 monoclonal antibody that binds specifically to human CD6 SRCR domain 1 (D1) and does not inhibit ALCAM binding to hCD6.

When varying concentrations of ALCAM-Fc was incubated along with a fixed concentration of T1h in a CD6-Fc coated ELISA plate, T1h was detected at all concentration of ALCAM-Fc. This experiment suggested that T1h binds to a different domain from the ALCAM binding domain (Domain 3).

When MEM 98, an antibody which binds to domain 1 [Castro A A M et al, *J of Immunol*, 178 (2007) 4351-4361.], is competed with T1h there is a dose dependent competition observed, suggesting that both bind to the same domain namely Domain 1.

In other aspects of the invention, methods are provided for modulating inflammatory conditions like multiple sclerosis, transplant rejection, Graft versus Host Disease (GvHD) and Type-1 diabetes. The T1h monoclonal antibody is able to inhibit naïve T cell proliferation as observed in a Mixed Lymphocyte Reaction, in a PHA mediated PBMC proliferation assay and finally PBMC proliferation in presence of tethered anti CD3 antibody and anti CD3 antibody+ALCAM-Fc. It reduces pro inflammatory cytokines and reduces expression of IL2 receptor (CD25) and CD4 on the cells.

Type 1 diabetes is insulin dependent and is considered an autoimmune disease mediated by T cells. This would suggest that the T1h antibody has the function to prevent islets β cells depletion by interfering with the proliferation of autoreactive T cells. If the mass of these cells are intact then it would lead to reduced dependence to insulin. Hence it is possible that in keeping with the action profile of the T1h antibody, it may be effective in Type 1 diabetes by promoting an anti-inflammatory response in combination with insulin, Glutamic acid decarboxylase (GAD) and Heat Shock Protein 60 (HSP60). By extending the same logic it would be reasonable to assume that the molecule may work more effectively with a Glucagon like Peptide-1(GLP1) or its related mimic Exendin-4 maybe in an additive or even in a synergistic fashion. GLP-1 and Exendin-4 augment glucose mediated insulin release, decrease levels of glucagons and increase β cells by inhibiting apoptosis and promoting neogenesis of these cells.

T1h may be effective in Multiple Sclerosis in combination with Myelin Basic Protein (MBP) or Myelin oligodendrocyte glycoprotein (MOG).

Also T1h in combination with other small molecules which play anti-inflammatory and immune-suppressive roles like Sirolimus, Tacrolimus and Mycophenolate Mofetil can have specific therapeutic benefits in Auto-immune disorders, Transplant Rejection and GvHD.

These methods include administration to a patient of a therapeutically or pharmaceutically effective amount of an anti-CD6 binding agent that binds specifically to human CD6 SRCR domain 1 (D1) and does not inhibit ALCAM binding to hCD6. Preferred anti-CD6 binding agents for use in these methods are monoclonal antibodies, including humanized and human monoclonal antibodies, as well as modified immunoglobulins such as antibody fragments and mutagenized forms of native antibodies having substantial amino acid sequence identity with a corresponding native antibody, and sharing substantially the same binding specificity therewith.

In yet additional aspects of the invention, diagnostic compositions and methods are provided for detecting CD6, $CD6^+$ cells, and/or CD6-mediated activity, for example CD6 activity related to T cell activation, in in vitro and in vivo assays. These methods likewise employ anti-CD6 binding agents that bind specifically to human CD6 SRCR domain 1 (D1) and does not inhibit ALCAM binding to hCD6.

The various functional characteristics of the subject antibody of the present invention can be screened using a variety of methods, including but not limited to those that use in vitro assays, in vivo and cell-based assays, and selection technologies. Multiple properties may be screened simultaneously or individually. Proteins may be purified or not purified, depending on the requirements of the assay. In one embodiment, the screen is a qualitative or quantitative binding assay for binding of anti-CD6 antibodies to a protein molecule that is known or thought to bind the anti-CD6 antibody. Such assays often involve monitoring the response of cells to anti-CD6 antibody, for example cell survival, cell death, cellular phagocytosis, cell lysis, change in cellular morphology, or transcriptional activation such as cellular expression of a natural gene or reporter gene. For example, such assays may measure the ability of anti-CD6 antibodies to elicit ADCC or CDC. For some assays additional cells or components, that is in addition to the target cells, may need to be added, for example serum complement, or effector cells such as peripheral blood monocytes (PBMCs), NK cells, macrophages, and the like.

Optimal dosages and dosage regimens to be administered may be readily determined by those skilled in the art, and will vary with the pharmacodynamic characteristics of the particular agent, its time and mode of administration, the strength of the preparation and the advancement of the disease condition (including the nature and extent of the symptoms of the disease). In addition, factors associated with the particular patient being treated, including patient's sex, age, weight, diet, physical activity and concomitant diseases, will result in the need to adjust dosages and/or regimens. The pharmaceutically effective dose is 0.1-25 mg/kg/week.

The biological properties of the anti-CD6 antibodies of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties.

The foregoing description of the invention illustrates and describes the present invention. Additionally, the disclosure shows and describes representative preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described herein below are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

1. Nucleotide (Both Genomic and Plasmid) and Amino Acid Sequence of T1h

Multiple PCR reactions using genomic and plasmid DNA as the template were used to determined the nucleotide sequence of T1h. Genomic DNA was prepared from NSO cells expressing T1h. Amino acid sequence was determined using ESI-TOF and MALDI-TOF. Peptide mapping using different enzymes, including trypsin, Lys-C and Glu-C were used to evolve the final amino acid sequence. The sequence disclosed in FIG. 1 is slightly different from the already published sequence of T1h in U.S. Pat. No. 5,712,120, its equivalent EP 0699755, U.S. Pat. No. 6,572,857 and its equivalent EP 0807125. It has been established that the sequence disclosed in this patent has full functional activity on its target CD6 as mentioned in the numerous examples mentioned below.

2. T1h Binds to Domain 1 (D1) of CD6 Receptor

The ELISA experiment clearly showed that presence of ALCAM in varying concentrations does not prevent T1h from binding to CD6-Fc. The absence of competition between ALCAM and T1h suggests that the binding domains for the two are different.

When MEM 98, an antibody which binds to domain 1 (D1) (Castro A A M et al, *J of Immunol,* 178 (2007) 4351-4361.), is competed with T1h there is a dose dependent competition observed, suggesting that both bind to the same domain namely Domain 1.

3. T1h does not Induce Apoptosis in HUT 78 Cells

One of the hallmarks of apoptosis is the translocation of phosphotidylserine (PS) from the inner part of the plasma membrane to the outside [*J Biol Chem* 1990. 265: 4923-4928]. The analysis of phosphotidyl serine on the outer leaflet of apoptotic cell membranes is performed by using Annexin-V-Fluorescein and Propidium iodide (PI) for the differentiation of apoptotic and necrotic cells. Annexin V is a $Ca^{2+}$ dependent phospholipid binding protein with a high affinity for phosphotidyl serine [*J Immunol Methods* 1995. 184: 39-51]. While PI binds to distinct necrotic cells, Annexin-V-Fluorescein binds to apoptotic cells. This method helps in distinguishing the apoptotic and necrotic cell populations. The early apoptotic population is only Annexin V positive while the late apoptosis is both Annexin V and PI positive.

In this experiment we observe that T1h has limited apoptotic potential in HUT78 cells, a T lymphoma cell line expressing CD6. The HUT 78 cells treated with the T1h, showed 40% of apoptosis which is almost equal to the untreated control in the Annexin V FITC channel. The untreated and the nonspecific isotype control, hR3 (a monoclonal antibody binding to EGFR) treated cells showed 35.3% and 36.5% apoptosis respectively while the positive control rapamycin showed 54.3% apoptosis. This data suggest that T1h does not mediate apoptosis in HUT 78 cell line.

4. T and B Cells Positive for CD6, show Difference in Expression of CD6 Receptors.

Thymocytes, mature T cells, a subset of B cells called B-1 subtype and some cells of the brain express CD6 [*J Exp Med* 1991. 174: 949-952; *J Immunol* 1997. 158: 1149-1156]. The aim of the experiment is to quantify receptor density and difference in expression of CD6 in T and B cells respectively.

The experiments suggest that CD6 receptor density is 10 fold more on the T cells as compared to the B cells. The method does not claim to quantify absolute receptor density as saturating quantities of antibodies were not used. However the fold difference in expression pattern in T and B cells is definitely discernable.

5. T1h Induces Mild ADCC (Antibody Dependent Cell Mediated Cytotoxicity)

When antibody binds to the target or infected cells, the Fc portion of the antibody binds to Fc receptors present on the surface of cells particularly Natural Killer (NK) cells. This then causes the activation of these cells. These activated cells release cytokines and cytotoxic granules and promote cell death by triggering apoptosis. This is known as antibody dependent cell mediated cytotoxicity (ADCC).

In the instant invention, the target cell population (HUT 78/Daudi) is labeled with cell tracking dye CFSE (Carboxyfluorescein diacetate succinimidlyl ester). The fluorescein based dye CFSE has biochemical properties which makes it particularly well suited for live cell labeling [*J Immunol Methods* 2000. 243: 147-154]. CFSE consists of fluorescein molecule containing two acetate moieties and a succinimidyl ester functional group. In this form it is membrane permeable and non fluorescent. After diffusion into the intracellular environment, endogenous esterases remove the acetate groups, rendering the molecule highly fluorescent and non-permeable to the cell membrane [*J Immunol Methods* 2000. 243: 147-154] The target cells, HUT 78 cells, are incubated in the presence or the absence of the antibody, T1h. The effector cells (are PBMCS harvested by Ficoll paque method) are added at different ratios (Target: effector; 1:1, 1:25, 1:50, 1:100) and incubated at 37° C. for optimal time. 7AAD is used to measure cell death. 7 amino actinomycin D (7AAD) enters the dead cells and binds to DNA. CFSE labeled cells are gated to evaluate the Antibody mediated cellular cytotoxicity of the target cells. Daudi cells were used to qualify the assay using Rituxan which is well known to have potent ADCC activity. Rituxan showed greater that 50% cytotoxicity in 6 hours. Under similar conditions, four independent experiments suggested that T1h induces mild ADCC in HUT 78 cells, with overnight incubation in presence of effector cells.

6. T1h does not Mediate Complement Dependent Cytotoxicity (CDC)

The Alamar Blue (Resazurin) based assay is used to measure the ability of an antibody to promote cell killing. This is induced by the binding of the antibody to a cell surface antigen thereby fixing and activating complement resulting in target cell lysis. Resazurin is a redox-active dye which when reduced, changes colour from blue to pink. Recent data would suggest that resazurin enters the cytoplasm of the cells where it was reduced to the fluorescent product and then excreted again back to the medium [*Eur J Biochem* 2000. 267: 5421-5426].

The results from these experiments conclusive prove that the antibody does not induce CDC in a cell line expressing CD6 namely HUT 78.

7. T1h Inhibits PITA Mediated Lymphocyte Proliferation

Phytohemagglutinin (PHA-M) is used for the stimulation of cell division in lymphocyte cultures. PHA, the lectin extract from the red kidney bean (Phaseolus vulgaris), contains potent, cell agglutinating and mitogenic activities [*Prot Natl Acad Sci USA* 1982. 79: 1611-1615]. PHA contains a family of five iso lectins ($L_4E_0$, $L_3E_1$, $L_2E_2$, $L_1E_3$, $L_0E_4$) each being a tetramer held together by non covalent forces. The subunits are of two different types, designated leukocyte reactive (L) and erythrocyte reactive (E). L has high affinity for lymphocyte surface receptors but little for those of erythrocytes and is responsible for the mitogenic properties of isolectins. E is responsible for erythrocyte agglutinating properties. PHA-P is the protein form and PHA-M is the mucoprotein from of these isolectins [*J Biol Chem* 1977. 252: 9018-9023].

The PBMCs are labeled with the cell tracking dye CFSE (Carboxyfluorescein diacetate succinimidlyl ester). Then cells are incubated with or without antibody at various concentrations. The cells are stimulated by Phytohemagglutin (PHA) to proliferate for three days at 37° C. As the cells proliferate, CFSE is distributed equally to the daughter cells, each successive generation will have half of the cellular fluorescence intensity [*J Immunol Methods* 1994. 171: 131-137]. The percentage of inhibition of proliferation is considered as the effect of the antibody. The % of inhibition of proliferation is estimated by the following formula [{PHA−(T1h+PHA)}/PHA]*100, where, PHA is proliferation induced by PHA, T1h+PHA is proliferation induced in presence of T1h and PHA.

These data suggest that T1h antibody mediates the inhibition of proliferation of PHA stimulated lymphocytes in a dose dependent manner. The percentage of inhibition may be varied among the individuals due to inherent variation among normal individuals. However overall, a dose dependent inhibition of PHA stimulated lymphocytes was observed with T1h but not with a non specific IgG1 isotype antibody hR3.

8. T1h Inhibits PHA Mediated Lymphocyte Proliferation even in a 96 Well Plate Based Alamar Blue Assay The previous experiment was altered to a high throughput plate based assay wherein the freshly harvested PBMC's are incubated in 96 well dishes with or without T1h or a non specific IgG1 isotype antibody hR3. Subsequently PHA is added to stimulate the proliferation of lymphocytes for three days. Proliferation is measured by using Alamar Blue. Test of Significance is done by T Test.

This assay reiterates the fact that PHA mediated proliferation of lymphocytes is significantly inhibited in presence of soluble T1h but not in presence of a non specific IgG1 isotype antibody hR3. This along with the previous experiment would suggest a role for T1h in inhibiting naïve T cell proliferation.

9. T1h Reduces Proliferation of Lymphocytes Induced by Tethered anti CD3, Anti CD3+ T1h and antiCD3+ALCAM Fc It is known that stimulation through the T cell receptor (TCR) and co stimulatory receptors triggers a switch in T cell differentiation from a quiescent (resting) state to an activated state characterized by rapid rates of growth and proliferation and the acquisition of effector function [*Immunity* 2007. 27: 173-178]. The human CD6 receptor is a type 1 glycoprotein of 105-130 kDa expressed on immature thymocytes, mature T and a subset of B lymphocytes called the B1a subset, chronic B cell lymphocytic leukemia and various regions of the brain [*J Immunol* 2006. 177: 1152-1159]. CD6 is a group B member of the scavenger receptor cysteine rich (SRCR) superfamily of protein receptor based on the presence of in the extracellular region of three 100 to 110 aa long cysteine rich domains characteristic of the family [*J Exp Med* 1991. 174: 949-952]. Available evidence indicates that CD6 is an accessory molecule involved in the modulation of lymphocyte activation and differentiation processes [*J Immunol* 2006. 177: 1152-1159]. On thymocytes and resting mature T cells, CD6 partially associates with the TCR/CD3 complex [*J Immunol* 2004. 173: 2262-2270] and with CD5, a close member of the SRCR superfamily [*J Biol Chem* 2003. 278: 8564-8571]. Moreover, CD6 accumulates at the central part of the mature immunological synapse (IS), where it co-localizes with the TCR/CD3 and CD5. CD6 has also been implicated in early T cell-APC contacts influencing IS maturation and also T cell proliferative responses [*J Inununol* 2006. 177: 1152-1159, *Eur J Immunol* 2004. 34: 930-940].

It is well established that optimal T cell activation leading to cell proliferation requires at least two stimulatory signals. One involves the TCR-CD3 complex which recognizes peptide fragments bound to either Major histocompatibility complex (MHC) class I or Class II molecules on Antigen Presenting Cells (APC) the second signal which is not antigen-specific, has been termed the co stimulatory or accessory signal, because, although essential, it does not cause T cell proliferation by itself [*Immunology* 1998. 93: 358-365]. Several potential co-stimulatory signal receptors and their ligands have been identified and these include the interactions between CD4 with Class II MHC, CD8 with Class I MHC, CD2 with lymphocyte function-associated antigen-3, CD5 with CD72, CD28 with B7-1/B7-2 and also CD6 with CD6 ligand (D166 or ALCAM) [*Immunology* 1998. 93: 358-365; *Curr Opin Immununol* 1995. 7: 389-395].

Previous literature exists on the effect of tethered Anti CD3 antibody with or without anti co-stimulatory molecule antibody leads to lymphocyte proliferation. Upon CD3 stimulation, either alone or by co-cross-linking with CD2 or CD4, CD6 becomes transiently phosphorylated on the two most C-terminal tryosine residues (Y629 and Y662) [*J Exp Med* 1993. 177: 219-223]. Accordingly, it has been show that the CD6-mediated effects on T cell proliferation involve a tyrosine kinase activity, which is dependent on PKC activation [*Cell Immunol* 1995. 166: 44-52]. Although the signaling pathway of CD6 is less well characterized compared to that of CD28, another co-stimulatory molecule, there are some similarities between the effects of these two cell surface antigens. For, instance, ligation of either one of the two receptors synergized with signals via the TCR complex to enhance T-cell proliferation [*J Immunol* 1989. 143: 2439-2447]. They are also capable of triggering T-cell proliferation in the presence of Tissue Plasminogen Activator (TPA) resulting in the up-regulation of IL-2 receptors (IL-2R) and IL-2 mRNA [*Cell Immunol* 1995. 166: 44-52, *Proc Natl Acad Sci USA* 1989. 86: 1333-1337]. It is also shown that tethering Anti CD6 and Anti CD28 antibody caused proliferation of resting lymphocytes independent of stimulation by anti CD3 antibody [*Immunology* 1998. 93: 358-365]

In the instant invention we show that soluble T1h antibody inhibits T cell proliferation mediated by tethered Anti CD3, Anti CD3+T1h and anti CD3+ALCAM Fc. In fact we observe that the combination of Anti CD3+T1h and Anti CD3+ALCAM is in fact synergistic over anti CD3 alone as observed in a Bliss analysis of the data. We further show that addition of extraneous IL2 (1.25 ng/ml) causes partial recovery from soluble T1h mediated T cell proliferation inhibition. By cytokine analysis we show that T1h predominantly inhibits IFN γ, IL10 and TNF and extraneous addition of IL2 induces partial recovery of these pro-inflammatory cytokines. Estimation of receptor density of CD25 and CD4 in proliferating lymphocytes suggested that soluble T1h causes downregulation of both these markers while extraneous IL2 partially recovers these marker expressions. Taken together this data suggests that T1h inhibits T cell proliferation by inhibiting proinflammatory cytokines like IFN γ and decrease of IL2 Receptor expression. Since addition of extraneous IL2 shows partial 'gain of function' our results seem to suggest that T1h may be inhibiting IL2 synthesis mediated by tethered Anti CD3, Anti CD3+Tethered T1h and anti CD3+Tethered ALCAM Fc.

9a. Titration of IL2 in naïve PBMCs (Peripheral Blood Mononucleated Cells)

IL2 is a cytokine which is necessary and sufficient for T cell activation. It signals through the IL2 Receptor which it upregulates. It has a critical role in T cell development, T cell immunologic memory and the development of T regulatory cells. [*J Immunol* 1995. 155: 1151-1164]. From this experiment an optimal concentration of IL2 at 1.25 ng/ml was used in further experiments.

9b. T1h Causes Reduction of Proinflammatory Cytokines, CD4 and CD25 Receptor Expression without Inducing Apoptosis and this Inhibition is Partially Removed in Presence of Extraneous IL2.

Flow cytometry is an analytical tool that allows for the discrimination of different particles based on size and colour. The BD™ CBA employs a series of particles with discrete fluorescence intensities to simultaneously detect multiple soluble analytes. The BDA™ CBA is combined with flow cytometry to create a powerful multiplexed assay. The BDA CBA Human Th1/Th2 Cytokine II is used to quantitatively measure Interleukin-2, Interleukin-4, Interleukin-6, Interleukin-10, TNF and Interferon gamma levels in a single sample [*J Immunol Methods* 2001. 254: 109-118].

Six bead populations with distinct fluorescence intensities have been coated with capture antibodies specific for IL-2, IL-4, IL-6, IL10, TNF and IFN-γ proteins. The six bead populations are mixed together to form the BD™ CBA that is resolved in the FL3 channel of a DAKO CyanADP brand flow cytometer. The cytokine capture beads are mixed with the PE-conjugated detection antibodies and then incubated with recombinant standards or test samples to form sandwich complexes. Following acquisition of sample data using the flow cytometer, the sample results are generated in graphical and tabular format.

From these experiments it is clear that T1h causes inhibition of naïve T cell proliferation and this is mediated by substantial decrease in pro inflammatory cytokines and also reduction in CD25 and CD4 counts. Addition of exogenous IL2 is able to recover the inhibition as well as increase expression of the pro inflammatory cytokines and also increase absolute receptor counts of both CD4 and CD25. These results would suggest that the inhibition of T cell proliferation by T1h is mediated by suppression of IL2 and addition of exogenous IL2 causes a "gain of function". We also observe that the reduction in T cell proliferation is not mediated by induction of apoptosis.

10. T1h does not Inhibit Memory T Cell Proliferation.

After recognizing a foreign antigen on Antigen Presenting Cells, T cells proliferate and mount an immune response. Some of these T cells transform into memory T cells which are in circulation in the system and when challenged again with the same antigen, these cells proliferate and mount an immune response. Most humans are immunized to Tetanus Toxoid and when T cells from them are challenged with the same antigen, the memory T cells in the population proliferate. The experimental results show that Tetanus Toxoid do stimulate the proliferation of T cells in a dose dependent manner, but the sT1h does not show any inhibition of proliferation of these cells. This strongly suggests that T1h does not inhibit memory T cell proliferation. This is favorable for T1h therapy because circulating memory T cell proliferation is not affected and patients on T1h therapy would not become susceptible to infection.

11. T1h Inhibits T Cell Proliferation in a Mixed Lymphocyte Reaction Mediated by PBMCs and Raji Cells.

When mixtures of lymphoid cells from genetically disparate individuals are cultured in vitro they undergo a characteristic response which has been termed the mixed lymphocyte reaction (MLR) [*Prot Natl Acad Sci USA* 1973.70: 2707-2710]. This reaction is typified by an early proliferative phase followed by appearance of effector lymphocytes exhibiting specific cytotoxicity for target cells bearing antigens used to stimulate the original reaction.

Both populations of allogenic T lymphocytes proliferate in an MLR unless one population is rendered unresponsive by treatment with mitomycin C or lethal X-irradiation. In the latter system called a one way MLR, the unresponsive population provides stimulator cells that express alloantigens of the stimulator cells. In a one way MLR responder $T_H$ cells recognize allogenic class II MHC molecules on the stimulator cells and proliferate in response to these differences. Removal of the CD4+$T_H$ cells from the responder population with anti CD 4 plus complement abolishes the MLR and prevents generation of CTLs. Accessory cells like macrophages have also been shown to be important for MLR. It is now realized that the role of macrophages is to activate the class II-MHC restricted $T_H$ cells whose proliferation is measured in MLR.

In the instant invention one way MLR is performed with Raji cells treated with mitomycin thus they are the antigen presenting cells while proliferation is measured on PBMCs. Previous literature showed that Raji cells express ALCAM [*J Immunol* 2004. 173: 2262-2270].

From this experiment it is concluded that T1h specifically inhibits one way MLR where Raji cells are the Antigen presenting Cells and PBMCs proliferate.

12. T1h Inhibits T Cell Proliferation in a Mixed Lymphocyte Reaction Mediated by PBMCs and Mature Dendritic Cells In an allogeneic (Antigen Presenting Cells taken from one individual and the PBMCs taken from another individual) Mixed Lymphocyte Reaction, wherein mature Dendritic cells (Antigen Presenting Cells) cause proliferation of naïve PBMCs, T1h inhibits this proliferation in a dose dependent manner. The data showed that the mode of action involved down regulation of at least two major pro-inflammatory cytokines, namely IL6 and IFNγ.

Materials and Methods

Cell Lines and Cell Culture:

HUT 78 (T cell lymphoma Human cell line from ATCC) are used as target cells. Cells are cultured in Iscove's DMEM supplemented), which contains 2 mg/ml of $NaHCO_3$, 20 mM Hepes, 2 mM L-Glutamine and 20% FBS (Invitrogen).

Daudi cells (B cell Lymphoma, ATCC), cells are cultured in RPMI 1640; which contains 2 mg/ml of $NaHCO_3$, 20 mM Hepes, 2 mM L-Glutamine and 10% FBS (Invitrogen).

WIL2S cells (B cell lymphoma): Cells are cultured in DMEM; which contains 2 mg/ml of $NaHCO_3$, 20 mM Hepes, 2 mM L-Glutamine and 10% FBS (Invitrogen).

PBMC (Peripheral blood mononuclear cells) were used as Effector cells: PBMCs are isolated by Ficoll-Paque (Amersham Cat No: 17-14403-03) mediated density centrifugation. Buffy coats are obtained from healthy donors and always harvested fresh. Cells are cultured in RPMI 1640 (Invitrogen), which contains 2 mg/ml of $NaHCO_3$, 20 mM Hepes, 2 mM L-Glutamine and 5% FBS (Invitrogen).

Antibodies:

The following anti-CD6 MAbs were used in vitro: Rituxan (Genentech) hR3 antibody (CIM, Havana, Cuba).

1×PBS (Invitrogen Cat no: 10010). Coating buffer ($NaHCO_3$—8.4 g, $Na_2CO_3$—3.56 g, in $H_2O$ 1000 ml pH 9.5)

PBS/Tween (0.5 ml of Tween-20, SIGMA in 1000 ml of PBS)

Blocking solution (1% BSA in PBS)

RPMI 1640 (Cat No: 11875 Invitrogen)

Iscove's DMEM (Invitrogen Cat No: 12200-036)

Alamar Blue (Invitrogen DAL-1100)

Biotek Plate reader (Synergy™ HT)

Pooled human serum

Peripheral Blood form Healthy individual collected in EDTA vacutainers (BD vaccutainer cat no: 368457)

Iscove's DMEM Media (Invitrogen) supplemented with 1% FBS (Fetal bovine Serum)

Apoptosis KIT-Cat. No 1 988 549 (Roche)

Flow cytometer: Dako Cyan ADP

Ficoll-Paque (Amersham Cat No: 17-14403-03), RPMI 1640 Cat no: 11875 (Invitrogen), FBS. (Fetal Bovine Serum) Gibco Cat no:10082-147

Anti CD6-PE, Anti CD6-FITC, Anti D19-PECy5, Anti CD3-FITC and Anti CD4-Alexa AbD Serotec, UK)

SPHERO™ Rainbow calibration Particles (Cat no: RCP-30-5A)

CFSE (Sigma Cat no: 21888), 7AAD (Invitrogen Cat no: V 35124).

RPMI 1640 (Invitrogen), which contains 2 mg/ml of $NaHCO_3$, 20 mM Hepes, 2 mM L-Glutamine and 5% FBS (Invitrogen).

96 well Fluotrac 600 plate-Cat no. 655077 (Greiner Bio)

The following examples are offered by way of illustration, not by way of limitation.

EXAMPLE 1a

T1h and ALCAM does not Bind to the Same Domain by ELISA

The rhCD6FC/Chimera (R and D systems) (100 μg/ml) was diluted in coating buffer and 100 μl was added to each well of a 96 well Nunc-Maxisorp plate. The plate was then incubated at 4° C. overnight. The Plate was washed thrice with PBS Tween 20. Subsequently, 200 μl of blocking solution (2% BSA+0.1% Tween 20 in 1×PBS) was added and incubated for 1 hour at 37° C. After incubation, the plate was washed again with PBS Tween thrice, followed by the addition of T1h monoclonal antibody (0.2 mg/ml) and .rhALCAMFc (R and D systems) at varying concentrations. This was then incubated for an hour at 37° C. The plate was washed 3 times subsequently with PBS Tween. To the wells 200 μl of anti human IgG $(Fab)_2$ ALP (1:20000) diluted in blocking buffer was added and incubated for 1 hour at 37° C. The plate was washed thrice with PBS tween and 200 μl of p-Nitrophenyl Phosphate (PNPP) substrate is added to each well and incubated at 37° C. till colour develops around 15 minutes. Reading was taken at 405 nm using a BIOTEK Micro Plate Reader. The experiment indicates that the presence of ALCAM in varying concentrations does not prevent T1h from binding to a CD6 receptor. The absence of competition between ALCAM and T1h suggests that the binding domains for the two are different (FIG. 2)

EXAMPLE 1b

T1h Binds to Domain 1 (D1) of CD6

When MEM 98, an antibody which binds to domain 1 (Castro A A M et al, *J of Immunol*, 178 (2007) 4351-4361.), is competed with T1h there is a dose dependent competition observed, suggesting that both bind to the same domain namely Domain 1 (FIG. 3).

EXAMPLE 2

T1h does not Induce Apoptosis in HUT78 Cells.

The cells were harvested and 1.5 ml of $3.3 \times 10^5$ cells/ml (final cells: $5 \times 10^5$ cells) was seeded in each 35 mm dish. Required amount of antibody was added to respective dishes to make a final concentration of (5 μg/ml). In the control dish, no antibody was added. As a positive control cells were incubated with rapamycin at a concentration of 1.2 μg/ml. Cells were incubated overnight at 37° C. in 5% $CO_2$ incubator. The cells were then transferred to FACS tube BD Falcon Cat No: 352054 and centrifuged at 1200 RPM for 5 minutes at Room temperature (RT). The supernatant was discarded and resuspended in 2 ml of PBS and centrifuged at 1200 RPM for 5 mints at RT. The supernatant was discarded and 100 μl of Annexin-V-Fluorescein labeling solution was added and incubated for 10-15 min at RT. The cells were washed with 2 ml of PBS and centrifuged at 1200 RPM for 5 minutes. The supernatant was then discarded. Cells were resuspended in 0.5 ml of PBS and acquired by flow cytometer (3000 cells were gated) with 488 nm excitation. Samples were read in FITC channel for Annexin V and PE Texas red channel for PI. Annexin V alone and PI alone samples in the rapamycin treated arm, were run to enable compensation.

The HUT 78 cells that were treated with the T1h showed 40% of apoptosis which is almost equal to the untreated control in the Annexin V FITC channel. The untreated and the nonspecific antibody (hR3 antibody) treated cells showed 35.3% and 36.5% apoptosis respectively while the positive control rapamycin showed 54.3% apoptosis. This data suggest that the T1h does not mediate apoptosis in the HUT 78 cells (FIG. 4).

EXAMPLE 3

Difference in Expression of CD 6 Receptors on T and B Lymphocytes from Normal Individuals.

PBMCs were isolated by Ficoll-Paque (Amersham Cat No: 17-14403-03), mediated density centrifugation. Buffy coats were obtained from healthy donors and always harvested fresh. PBMCs were then washed in PBS. The PBMCs were then resuspended in 5 ml of 1×PBS at a cell density of $1.5 \times 10^6$ cells/ml and 100 ul was added to each falcon tube. 10 μl of conjugated antibody (1:10 dilution) was added to the respective tube and vortexed, and then incubated at 4° C. for 30 minutes. After incubation, 2 ml of 1×PBS was added to each tube and then centrifuged at 1200 RPM for 5 minutes at RT. Supernatant was discarded and cells were resuspended in 0.5 mL of 1×PBS to acquire cells in the flowcytometer. The cells (Lymphocytes) were Gated for a required population (3000 cells) in FSC and SSC. SPHERO™ (Cat no: RCP-30-5A) Rainbow calibration Particles is also acquired along with the above tubes in same voltage settings. The fluorescence Mean Channel Number (i.e. relative brightness) for each peak was recorded. The Mean Channel Number was converted to Relative Channel Number using the following formula
  i. Relative Channel #=(R/4)log(Mean Ch #×10)
  ii. Where R=Resolution (i.e. 256)
A Graph was plotted the with the assigned MEF value for each peak vs. the Relative Channel Number on an Excel sheet to obtain a Calibration Graph as shown in FIG. 5. The RCN for the CD6 antibody on T and B cells was obtained, which was plotted on the Sphero calibration graph to quantify the CD6 receptor density on the individual cells of the various subsets of lymphocytes.

The formula which is derived from the graph to calculate the number of receptors on the lymphocytes were;
  a. FITC channel: $y=134.95 e^{0.0366x}$
  b. PE channel: $y=23.6 e^{0.0373 6x}$ CD6 receptor density is 10 fold more on the T cells as compared to the B cells. The difference in expression pattern in T and B cells was found to be discernible (FIG. 6).

EXAMPLE 4

T1h Causes Mild ADCC (Antibody Dependent Cell Mediated Cytotoxicity)

Target cell lines (HUT 78/Daudi) were harvested and washed in PBS twice. The cells ($2\times10^5$) were re-suspended in 1 ml of 0.25 μM CFSE concentration (titration of CFSE is required for each cell type to pick a concentration of CFSE which does not leak into the PE Cy5 channel). Cells were incubated for 10 minutes exactly at 37° C. 2 ml of RPMI, 5% FBS was added to stop the reaction. Cells were washed twice with 2 ml RPMI 5% FBS each to remove the CFSE. The target cell preparation was then re-suspended in RPMI medium at a cell density of $1\times10^5$ cells/ml and 100 ul ($10^4$ cells) was added to each falcon tube. 50 ul of antibody (5 ug/ml, 10 ug/ml) was added into respective tubes and incubated for 30 minutes at RT. PBMCs (effector cells) were then added at T/E ratios of 1:1, 1:25, 1:50 and 1:100 to the respective tubes. The final volume was made to 250 ul with media in each tube. Each tube was centrifuged for 2 min at 1200 rpm to promote cell to cell interaction and incubated at 37° C. for ADCC to occur. Daudi cells were incubated for 6 hours with Rituxan and run along with the samples as a positive control. Cells were then washed with 1×PBS. 100 ul of 7 AAD (6.25 ug/ml) was added and incubated at 4° C. for 15 minutes. Cells were washed with 1×PBS spun down at 1200 RPM at 4° C. for 5 minutes. The supernatant was discarded and cells were resuspended in 500 ul of 1×PBS. Cells were acquired at around 200 events/sec and viewed in the FITC and PE Cy 5 Channels of the flow cytometer. CFSE positive cells fluoresced between the second and third decade in the log scale with no spill into the PE Cy 5 channel. A total of 3000 FITC positive cells were gated for and in this population, percentage of cells showing 7AAD (PE Cy5 positivity) was evaluated (FIG. 7 and FIG. 8). Also included in the assay apart from non specific antibody control were Effector/target cells alone in the ratio 1:1, 1:25, 1:50 and 1:100. The % of apoptosis was taken as % of cells at the Top right quadrant in FITC/PEcy5 dot plot scatter. (FIG. 9)

EXAMPLE 5

ADDC by T1h on HUT 78

Based on example 4, ADCC assay was done in the same assay procedure to examine the effect of T1h on HUT 78. The cells were incubated from 4 hrs to overnight. The optimal and consistent result was obtained with overnight incubation.

Figure 11:
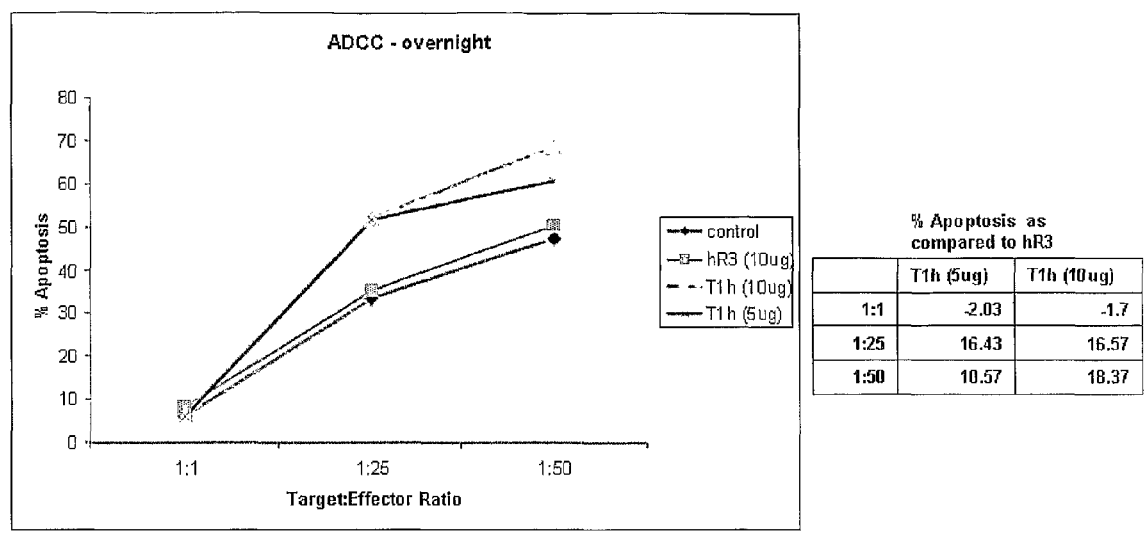
Figure 12:
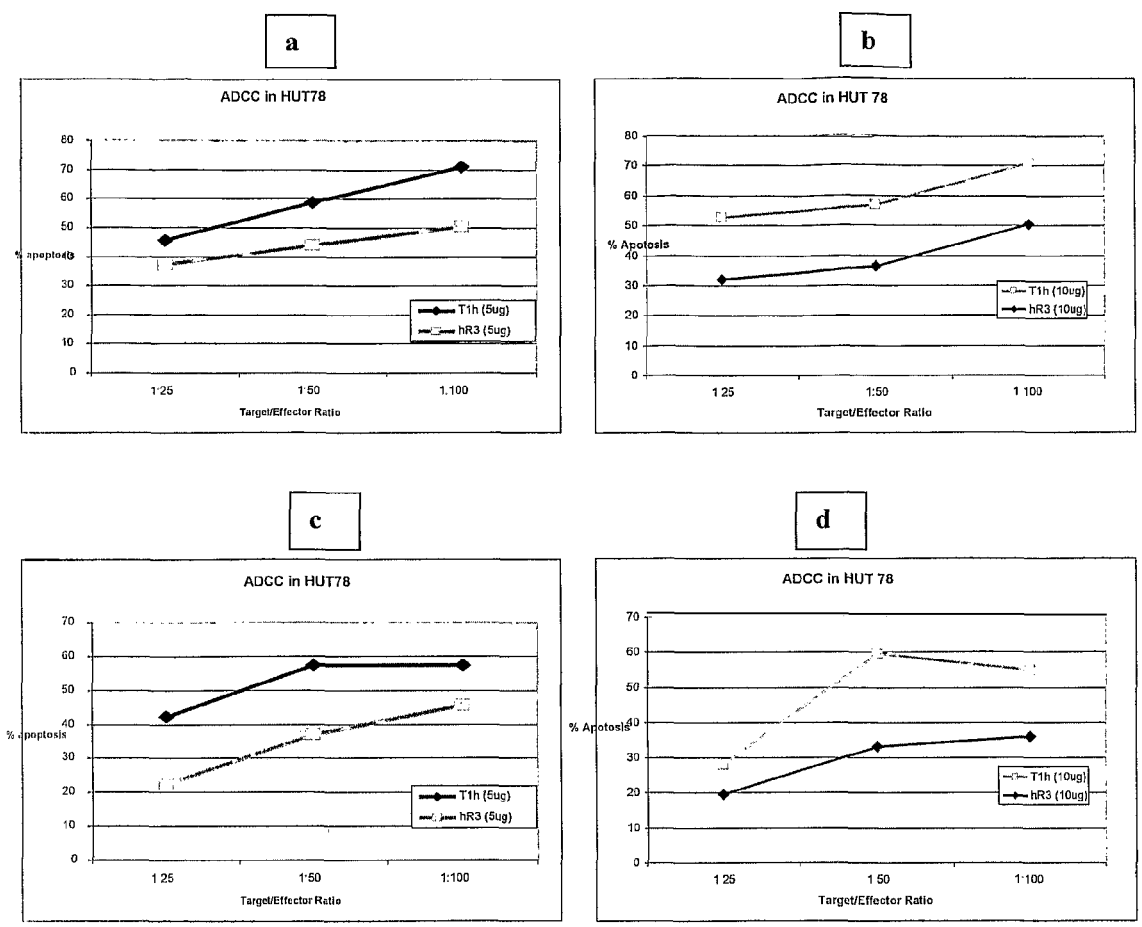

The in vitro results from four different individual experiments suggest that T1h induces mild ADCC in HUT 78 cells, with overnight incubation in presence of effector cells (FIGS. 10, 11, and 12)

EXAMPLE 6

T1h does not Mediate Complement Dependent Cytotoxicity (CDC)

Pooled human serum (minimum three) from whole blood was collected in sterile tube the blood was allowed to clot at room temperature for at least 4 hours and is centrifuged at 900 g for 20 minutes. The serum was harvested; aliquoted and stored at −80° C. Target cells (Wil-2S/HUT-78) were washed in dilution buffer and resuspended to $2\times10^5$ cells/mL. Antibody was diluted in dilution buffer at 4× of the final desired concentration. Complement was diluted at 4× the desired final concentration (i.e. 1:2.5 dilutions for a final concentration of 1:10). 50 μL each of diluted antibody, diluted complement and 50 μL of cell suspension (10,000 cells/well) were added to each well of a 96-well flat-bottom plate. The following control wells were included: target cells+Ab alone (spontaneous cell death), target cells+serum only (background lysis), and targets cells+10% SDS (for maximum cell death). The positive control was Wil-2S cells treated with Rituxan at different concentrations. 96-well plate was incubated for 2 hours at 37° C. 50 uL/well of Alamar Blue was added to each well, and the plate was incubated overnight at 37° C. Fluorescence is measured on a spectrophotometer Biotek Synergy™ HT with 530 nm excitation, 590 nm emission, and sensitivity=35. The results suggest that T1h does not induce CDC as compared to Rituxan (FIG. 13)

EXAMPLE 7

T1h Inhibits PHA Mediated Lymphocyte Proliferation.
Cell Lines and Cell Culture:
Whole blood was extracted from normal individuals after their consent following standard phlebotomy procedures. PBMC were isolated by Ficoll-Paque (Amersham Cat No: 17-14403-03) mediated density centrifugation. Buffy coats were obtained from healthy donors and always harvested fresh. Cells were cultured in RPMI 1640 (Invitrogen), which contains 2 mg/ml of $NaHCO_3$, 20 mM Hepes, 2 mM L-Glutamine and 10% FBS (Invitrogen).

Lymphocyte Proliferation Inhibition by Flow Cytometry Using CFSE

PBMCs were harvested and washed in PBS. The cells ($7.5\times10^6$) were re-suspended in 1 ml of 2 μM CFSE concentration in PBS. Cells were incubated for 10 minutes exactly at 37° C. 10 ml of RPMI, 10% FBS was added to stop the reaction. Cells were washed twice with 10 ml of PBS. The cell preparation was then re-suspended in 5 ml of PBS at a cell density of $1.5\times10^6$ cells/ml and 200 ul was added to each BD FACS tube. 200 ul of required and non specific antibody at various concentrations (50 ug/ml, 25 ug/ml, 12.5 ug/ml and 6.25 ug/ml respectively) were added and incubated for 30 minutes at 37° C. 2 ml of PBS was added to each tube and centrifuged at 1200 RPM for 5 minutes at RT to wash away the unbound antibody. 1 ml of RPMI, 10% FBS was added to the pellet in each tube. 1 ml of PHA 20 μg/ml in RPMI 10% FBS was added to the respective tube to stimulate the proliferation. The total volume in the tube is 2 ml and the final concentration of PHA was 10 μg/ml. The tube was vortexed and incubated for 3 day at 37° C. in $CO_2$ incubator. Cells were washed with PBS and spun down at 1200 RPM at 4° C. for 5 minutes. Supernatant were discarded and resuspended in 500 ul of 1×PBS. Total 20000 events were acquired at around 200 events/sec and viewed in the FITC channel.

% of Inhibition={[PHA−(T1h+PHA)]/PHA}*100

(Where PHA=PHA−cells alone

PHA+T1h=(PHA+T1h)−Cells alone

PHA+hR3=(PHA+hR3)−Cells alone)

Cells alone is CFSE+cells.

These data suggest that T1h antibody mediates the inhibition of proliferation of PHA stimulated lymphocytes in a dose dependent manner. The percentage of inhibition may be varied among the individuals due to inherent variation among normal individuals. However overall, a dose dependent inhibition of PHA stimulated lymphocytes was observed with T1h but not with a non specific antibody hR3 (FIG. 14, FIG. 15 and FIG. 16).

EXAMPLE 8

T1h Inhibits PHA Mediated Lymphocyte Proliferation Even in a 96 Well Plate Based Alamar Blue Assay PBMC's were freshly harvested and resuspended in RPMI 5% FBS at a concentration of $4\times10^5$ cells/ml. 50 µl of cells was added to each well. 100 µl of antibody (T1h or hR3) at 2× concentration (20 µg/ml) was added to the respective well. 100 µl of media alone was added to the non antibody wells. The plate was then incubated for half an hour at 37° C. 50 µl of PHA at a concentration 4× (20 µg/ml) was added to the respective wells to stimulate the proliferation of lymphocytes. In the remaining wells, 50 µl of media was added to make a final volume of 200 µl/well in all wells. The plates were incubated for three days in the $CO_2$ incubator at 37° C. 65 µl of Alamar blue was added to each well and incubated overnight in a $CO_2$ incubator at 37° C. Fluorescence was measured on a spectrophotometer Biotek Synergy™ HT with 530 nm excitation, 590 nm emission, and sensitivity=35.

Figure 17:
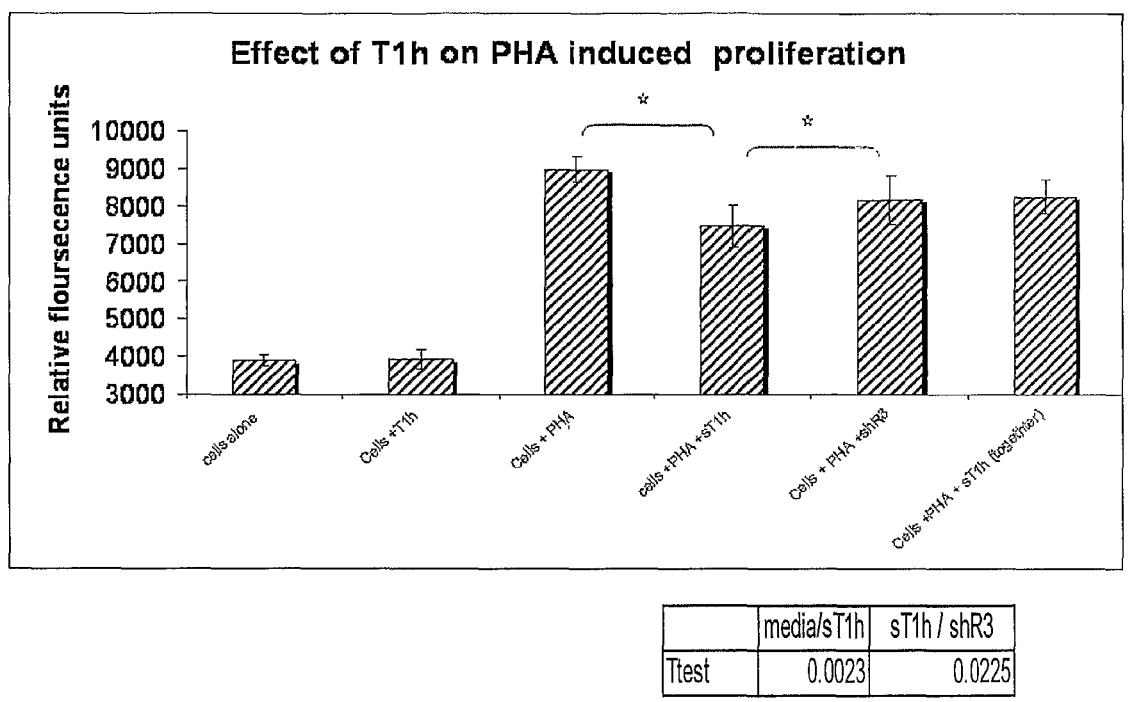

This assay reiterates the fact that PHA mediated proliferation of lymphocytes is significantly inhibited in presence of soluble T1h but not in presence of a non specific antibody hR3. This along with the previous experiment would suggest a role for T1h in inhibiting naïve T cell proliferation. This experiment also shows that the inhibition of PHA mediated T cell proliferation can be converted into a convenient plate based assay format as compared to the previous experiment which was Flow based (FIG. 17).

EXAMPLE 9

T1h Reduces Proliferation of Lymphocytes Induced by Tethered Anti CD3, Anti CD3+Tethered T1h and Anti CD3+ Tethered ALCAM Fc 50 µl of coating buffer was added to 96 well plate, 50 ul of anti CD3 antibody of 2× concentration (1 ug/ml) was added to the row A as in FIG. 18. 50 µl of antibody dilution from the first row A was taken and serially diluted down the plate upto row E using a 12 channel electronic pipette. 50 µl of coating buffer was added to 1-4 column of Row A-E., 50 µl of antibody (T1h (5-8) or ALCAM Fc (9-12)) of 2× (2 µg/ml) concentration was added to the respective wells, so that final concentration of the wells had constant 1 µg/ml of the antibody and the various concentration of anti CD3 antibody (row A-E had 1, 0.5, 0.25, 0.625 µg/ml) (FIG. 18). 100 µl of T1h or hR3 or ALCAM 1 µg/ml was added to the respective wells as control (as shown in the template). The above set was done in three plates, for the media control, sT1h and shR3. The plate was incubated at 4° C. overnight for the antibody to bind to the plate.

Blocking the Plate

The plate was brought to room temperature and the antibody in coating buffer was aspirated using vaccusafe (IBS Integra BioSciences), non-specific binding sites were blocked by adding 200 µl of blocking solution to each well. The plate was incubated at 37° C. for 1 hour and washed two times with PBS/Tween. The third wash was given with the RPMI media. The residual volume of media was removed carefully.

Add Cell Suspension:

100 µl PBMCs (30,000 cells) was added to each well. 100 µl of the required antibody (T1h or hR3) 2× concentration were added to the respective plates. 100 µl of the media were added in the media plate. The 96 well plates were incubated for 72 hours at 37° C. in the 5% $CO_2$ incubator. 65 µl of Alamar Blue solution was added to each well and incubated overnight at 37° C. in the 5% $CO_2$ incubator. The fluorescence using a 96 well fluorimeter (Synergy HT with Gen 5 software) was read with excitation at 530 nm and emission at 590 nm (Sensitivity=35) (FIG. 19).

The combination of tethered anti-CD3+T1h and anti CD3+ ALCAM is synergistic over tethered anti-CD3 alone with respect to Bliss analysis (FIG. 20).

EXAMPLE 9a

Titration of IL2 in Naïve PBMC's

100 µl of media was added to all the wells. 100 µl of 2× concentration of IL 2 (20 ng/ml) was added to the first row A2 to A10. From the first row 100 µl was taken to do a serial dilution down the plate till row H. 50 µl of the PBMCs suspension ($6\times10^5$ cells/ml) was added to all the wells. 50 ul of the media or antibody (T1h or hR3 10 µg/ml) or PHA 10 µg/ml was added in the respective well to make a final volume of 200 µl. The plate was incubated for 5 days at 37° C. in the 5% $CO_2$ incubator. 65 µl of Alamar Blue solution was added to each well and incubated overnight at 37° C. in the 5% $CO_2$ incubator. The fluorescence was read using a 96 well fluorimeter (Synergy HT with Gen 5 software) with excitation at 530 nm and emission at 590 nm (Sensitivity=35). Based on this experiment it was decided to choose 1.25 ng/ml of IL2 in subsequent experiments (FIG. 21).

EXAMPLE 9b

T1h Causes Reduction of Proinflammatory Cytokines and this Inhibition is Partially Removed in Presence of Exogenous IL2.

Cytokine Analysis

Preparation of Human Th1/Th2 Cytokine Standards 1 vial of lyophilized Human Th1/Th2 Cytokine standards was reconstituted with 0.2 ml of assay diluent to prepare a 10× bulk standard and allowed to equilibrate for at least 15 minutes before making dilutions. 12×75 mm tubes (BD Falcon Cat. No. 352008) were labeled and arranged in the following order: 1:2, 1:4, 1:8, 1:16, 1:32, 1:64, 1:128, and 1:256.

900 µl of assay diluent was pipetted to the top standard tube. 300 µl of assay diluent was pipetted to each of the remaining tubes. A serial dilution was performed by transferring 300 µl from the top standard to the 1:2 dilution tube and mixed thoroughly. Further serial dilutions were made by transferring 300 µl from the 1:2 tube to the 1:4 tube and so on to the 1:256 tube, and mixed thoroughly. One tube containing assay diluent was prepared to serve as the 0 pg/ml negative control.

Preparation of Mixed Human Th1/Th2 Cytokine Beads

The Capture Beads were bottled individually and it is necessary to pool the bead reagents (A1-A6) immediately before mixing them together with the PE Detection Reagent, standards and samples. The numbers of assay tubes (including standards and controls) that are required for the experiment were determined. Each Capture Bead suspension was vortexed for a few seconds before mixing. 10 µl aliquot was added of each Capture Bead, for each assay tube to be analyzed, into a single tube labeled "mixed Capture Beads" (e.g., 10 µl of IL-2 Capture Beads×18 assay tubes=180 µl of IL-2 Capture Beads required).

Preparation of Samples:

Test samples were diluted by the desired dilution factor (i.e., 1:2, 1:10, or 1:100) using the appropriate volume of assay diluent. The sample dilutions were mixed thoroughly before transferring samples to the appropriate assay tubes containing mixed Capture Beads and PE Detection Reagent Culture Supernatant Assay Procedure 50 µl of the mixed Capture beads (prepared using the procedure described in Preparation of Mixed Human Th1/Th2 Cytokine Capture Beads) were added to the appropriate assay tubes. The mixed Capture beads were vortexed before adding to the assay tubes. 50 µl of the Human Th1/Th2-II PE Detection Reagent was added to the assay tubes. 50 µl of the Human Th1/Th2 Cytokine Standard dilutions was added to the control assay tubes. 50 µl of each test sample was added to the test assay tubes. The assay tubes were incubated for 3 hours at RT and protected from direct exposure to light. 1 ml of Wash Buffer was added to each assay tube and centrifuge at 200×g for 5 minutes. The supernatant was carefully aspirated and discarded from each assay tube. 300 µl of Wash Buffer was added to each assay tube to resuspend the bead pellet. Samples were analysed on a flow cytometer (FIG. 22 and FIG. 23).

Soluble T1h Inhibits CD4 and CD25 Receptor Expression on Proliferating T Cells

The assay was set up as described in the tethering assay procedure i.e. the coating of the plate and the culturing of the PBMCs, mentioned in FIG. 18. The cells were taken from the 96 well plate into a BD falcon tube. 2 ml of 1×PBS is added to each tube and centrifuged at 1200 RPM for 5 minutes. The supernatant was discarded and 100 ul of 1×PBS was added to the cell pellet. 100 ul of cells were taken in each tube and 10 µl of Fluorchrome, conjugated Anti CD4 Alexa or Anti CD25 PE was added and incubated for 30 minutes at 4° C. After incubation, 2 ml of 1×PBS was added to each tube and then centrifuged at 1200 RPM for 5 minutes at RT. Supernatant was discarded. Cells are resuspended in 0.5 mL of 1×PBS and cells are acquired in the flowcytometer. The cells (Lymphocytes) were Gated for a required population (3000 cells) in FSC and SSC. Both percentage of cells and mean fluorescence intensity was estimated. This experiment was performed thrice and one representative figure is shown. The results were repeatable in independent experiments (FIG. 24).

No Increase in Apoptosis in the Above Mentioned Assay.

In the assay set up as described in the tethering assay procedure example 9, the cells were taken from the 96 well plate into a BD falcon tube and labeled for the apoptosis assay. 2 ml of 1×PBS was added each tube and centrifuged at 1200 RPM for 5 minutes. The supernatant was discarded and 100 ul of 1×PBS was added to the cell pellet. 100 ul of PI/annexin V labeling solution was added and incubated for 30 minutes at 4° C. After incubation, 2 ml of 1×PBS is added to each tube and then centrifuged at 1200 RPM for 5 minutes at room temperature. Supernatant was discarded. Cells were resuspended in 0.5 mL of 1×PBS and cells are acquired in the flow cytometer. The cells (Lymphocytes) are Gated for a required population (3000 cells) in FSC and SSC (FIG. 25).

From these experiments it is clear that T1h causes inhibition of naïve T cell proliferation and this is mediated by substantial decrease in pro inflammatory cytokines and also reduction in CD25 and CD4 counts. Addition of exogenous IL2 is able to recover the inhibition as well as increase expression of the pro inflammatory cytokines and also increase absolute receptor counts of both CD4 and CD25. These results would suggest that the inhibition of T cell proliferation by T1h is mediated by suppression of IL2 and addition of exogenous IL2 causes a "gain of function". We also observe that the reduction in T cell proliferation is not mediated by induction of apoptosis.

EXAMPLE 10

No Inhibition of Memory T Cells by T1h in a Tetanus Toxoid Mediated T Cell Proliferation Assay PBMCs were isolated by Ficoll-Paque (Amersham Cat No: 17-14403-03), density gradient centrifugation. Buffy coats were obtained from healthy donors and always harvested fresh. PBMCs were then washed in PBS (Invitrogen). The PBMCs were then re-suspended in 2 ml of RPMI media with 5% FBS supplemented at a cell density of $0.3 \times 10^6$ cells/ml. The cells were then incubated for 30 minutes with or without the T1h 10 ug/ml and hR3 which is used as nonspecific control in a sterile BD FACS 5 ml tube. After incubation, cells were vortexed and 100 µl of the cell suspension was added to the respective wells. 100 ul of the Tetanus toxoid (Cat #582231, CALBIOCHEM) (10 ug/ml) working solution (RPMI media with 5% FBS) was added to the respective wells to stimulate the memory T cell proliferation. The plates were incubated for five days in the $CO_2$ incubator at 37° C. 65 µl of Alamar blue was added to each well and incubated overnight in a $CO_2$ incubator at 37° C. Fluorescence was measured on a spectrophotometer Biotek Synergy™ HT with 530 nm excitation, 590 nm emission, and sensitivity=35 (FIG. 26).

The experimental results show that Tetanus Toxoid does stimulate the proliferation of T cells in a dose dependent manner, but the sT1h does not show any inhibition of proliferation of these cells. This strongly suggests that T1h does not inhibit memory T cell proliferation. This is favorable for T1h therapy because circulating memory T cell proliferation is not affected and patients on T1h therapy would not become susceptible to infection.

EXAMPLE 11

T1h Inhibits T cell Proliferation in a Mixed Lymphocyte Reaction Mediated by PBMCs and Raji Cells Raji/PBMCs cells were harvested and resuspended in 1×PBS. $8 \times 10^5$ cells/ml of Raji cells/PBMCs were resuspended in 1 ml of mitomycin (25 ug/ml). Cells were incubated for 30 minutes in a $CO_2$ incubator at 37° C. After Incubation 2 ml of RPMI with 5% FBS was added to each tube and centrifuged at 1200 RPM for 5 minutes at RT to remove the mitomycin. The supernatant was discarded and again 2 ml of RPMI with 5 FBS was added and centrifuged. Supernatant was discarded and cells are resuspended in the RPMI media 50 ul of PBMCs ($4 \times 10^5$ cells/ml) was added to the respective wells of 96 well round bottom plates. 100 µl of antibody dilution T1h or hR3 (10 ug/ml) was added to the respective wells and incubated for 30 minutes in a $CO_2$ incubator at 37° C. 50 ul of the Mitomycin treated Raji cells (4×10⁵ cells/ml) was added into the respective wells Along with the assay, controls which were included were Mitomycin treated Raji cells alone, PBMCs alone, Mitomycin treated Raji cells+ PHA, PBMCs+PHA, Mitomycin treated Raji and PBMCs. The plate was incubated for 5 days in a $CO_2$ incubator at 37° C. 65 μl of Alamar blue was added to each well and incubated overnight in a $CO_2$ incubator at 37° C. Fluorescence was measured on a spectrophotometer Biotek Synergy™ HT with 530 nm excitation, 590 nm emission, and sensitivity=35.

In conclusion it was observed that T1h can specifically inhibit one way MLR where Raji cells are the Antigen Presenting Cells and PBMCs proliferate (FIG. 27 and FIG. 28).

EXAMPLE 12

Mixed Lymphocyte Reaction (Dendritic Cells and Peripheral Blood Lymphocytes (PBLs):
MLR Assay:
MLR assay was performed as DC:PBL=1:2 ratio. The experiment template was designed with three concentrations of T1h with positive control Pimecrolimus and negative control hR3. The template is shown. (FIG. 29). Serial dilutions were done accordingly across the plate.

PBLs and or DCs were added as per plate layout. Mytomycin C treated PBLs were added to the corresponding wells in the plate. In all wells final volume was 200 ul. MLR was done in duplicates. One plate for Proliferation Assay & the other for Cytokine Assay. Finally both the plates were given a brief spin and kept in $CO_2$ incubator for 6 days.

Proliferation Assay:
After incubation the plate was checked for contamination under microscopy and 20 ul of alamar blue (10% of total volume per well) was added to each well. Readings were taken at sensitivity 35 at different time frames starting at 4 hours till overnight (FIG. 30).

Cytokine Assay:
Supernatant was collected from each well and for each group the supernatant was pooled. The cytokines were analyzed in flow cytometry using BD CBA Th1/Th2 kit II (FIG. 31).

In an allogeneic (Antigen Presenting Cells taken from one individual and the PBMCs taken from another individual) Mixed Lymphocyte Reaction, wherein mature Dendritic cells (Antigen Presenting Cells) cause proliferation of naïve PBMCs, T1h inhibits this proliferation in a dose dependent manner. The data showed that the mode of action involved downregulation of at least two major pro-inflammatory cytokines, namely IL6 and IFNγ.

EXAMPLE 13

Type I Diabetes Animal Model
NOD (Nonobese diabetic) female mice are known to develop spontaneous autoimmune T cell mediated diabetes, as measured by increased glucose, over time. This Insulin dependent diabetes mellitus (IDDM) model is an excellent model to study therapeutic and prophylactic effect of drugs. This mouse was used to study the therapeutic and prophylactic benefit of the surrogate antibody to CD6 (rat monoclonal which binds to murine CD6 in a similar fashion as T1h binds to human CD6).

In the pilot experiment, animals sourced from Harlan were shown to have developed the disease in 8-10 weeks. Age at the onset of the experiment of these mice is 6-7 weeks. Dose ranging from 2.46-19.68 mg/kg/week significantly reduced glucose levels and in fact at the highest dose reduced the glucose levels to normal.

A similar experiment in ten mice in a therapeutic setting delayed the onset of the disease in a dose dependent fashion. The delay was as much as three weeks at the highest dose.

EXAMPLE 14

Collagen Induced Arthritis model
The mouse model for collagen induced arthritis (CIA) is particularly advantageous to study rheumatoid arthritis in an animal model. The model is also used historically to study the effects of anti rheumatoid arthritis molecules including antibodies.

C57BL/6 male mice were used in the study. Briefly, chick collagen (CII) sourced from Sigma was dissolved in 10 mM acetic acid and filter sterilized using a 0.2 μm filter. 50 μl injection volumes were used in the study. CII was dissolved at 4 mg/ml for 100 μl volumes. All procedures were done at 2-8 C.

Heat killed Mycobacterium tuberculosis is finely ground in a mortar and pestle combined with incomplete Freund's adjuvant (IFA). The CII was then emulsified into this solution by mixing the two. All procedures were done at 2-8 C.

First dose is given at the base of the tail after two weeks a booster dose is injected. Development of arthritis is then monitored.

In ten mice which developed the disease, the surrogate anti CD6 antibody specifically detecting mice CD6 in a similar domain to T1h was used. Dose ranging from 2.46-19.98 mg/kg/week significantly reduced the rheumatoid arthritis in a dose dependent manner in these mice as compared to untreated controls. These experiments establish the fact that rheumatoid arthritis can be controlled by a surrogate antibody to T1h.

EXAMPLE 15

Autoimmune Encephalomyelitis (EAE)
Experimental autoimmune encephalomyelitis (EAE) is an animal model of brain inflammation. It is an inflammatory demyelinating disease of the central nervous system (CNS) and is studied as a model for human CNS demyelinating diseases including the disease of multiple sclerosis.

C57BL/6 mice are known to be susceptible to this disease when injected with rat Myelin Basic Protein and a boost protocol in which the mice were immunized with 200 μg rat MBP in CFA on days 0 and 17 followed by standard pertussis toxin. This protocol resulted in a monophasic moderate disease course starting on day 20 with the histological hallmarks of inflammation and axonal damage but no significant demyelination.

10 mice in the treatment arm were exposed to varying concentrations of the surrogate antibody to T1h which binds to a similar domain to mice CD6 as T1h does with human CD6. The dose ranged from 2.46-19.68 mg/kg/week. The treatment significantly controlled the disease as compared to the placebo population in a dose dependent manner especially at the highest dose.

EXAMPLE 16

Allogenic Graft
Skin graft can be rejected in a specific manner when skin from inbred mice from strain A is transplanted to mice B the skin first becomes vascularized between day 3 and Day 7. The vascularized skin then becomes infiltrated with lymphocytes, monocytes, neutrophils and other inflammatory cells. There is decreased vascularization of the transplanted tissue by 7-10 days and visible necrosis in 10 days.

This experiment was tried on twenty mice (BALBc-WT) which received skin grafts from C57BL6/WT mice. The skin was excised and grafted into the different BALBc mice using standard surgical procedure. Ten mice in the treatment arm were exposed to varying concentrations of the surrogate antibody to T1h which binds to a similar domain to mice CD6 as T1h does with human CD6. The dose ranged from 2.46-19.68 mg/kg/week. The first injection was given a week prior to the BALB c mice receiving the graft and continued for 6 weeks after.

The data seems to suggest that the skin grafts were tolerated more frequently in the mice receiving the drugs as compared to the untreated animals. In all the untreated animals the grafts became necrotic within three weeks. The tolerance to the graft was also dose dependent with the animals receiving the highest dose sustaining the grafts more.

We claim:

1. A monoclonal anti-CD6 antibody that binds to domain 1 (D1) of CD6 and inhibits T cell proliferation without interfering with ALCAM binding, wherein the monoclonal antibody comprises heavy and light chain variable regions comprising amino acid sequences as set forth in Sequence ID No. 1 and 2, respectively, encoded by nucleotide sequences as set forth in Sequence ID Nos. 3 and 4 respectively, and effectively treats a disorder selected from a group consisting of multiple sclerosis, transplant rejection, rheumatoid arthritis, and psoriasis.

2. A monoclonal anti-CD6 antibody comprising heavy and light chain variable regions as set forth in Sequence ID No 1 and 2, respectively, wherein the monoclonal antibody treats a disorder selected from a group consisting of multiple sclerosis, transplant rejection, rheumatoid arthritis, and psoriasis and exhibits at least one of the following functions:
   inhibits proliferation of naïve PBMCs induced by tethered anti-CD3;
   inhibits one way MLR where Raji cells are Antigen Presenting Cells and PBMCs proliferate;
   inhibits one way autologous MLR mediated by PBMCs;
   inhibits T cell proliferation by mediating suppression of IL2; and
   inhibits naive T cell proliferation by reducing CD25 and CD4 counts.

3. A method of treatment of a disorder selected from a group consisting of multiple sclerosis, transplant rejection rheumatoid arthritis, and psoriasis, said method comprising the step of administering the monoclonal anti-CD6 antibody according to claim 1, in an effective dose from 0.1-25 mg/Kg/week.

4. A monoclonal anti-CD6 antibody comprising heavy and light chain variable regions as set forth in Sequence ID No 1 and 2, respectively and encoded by nucleotide sequences as set forth in Sequence ID Nos. 3 and 4, respectively and used for treatment of a disorder selected from a group consisting of multiple sclerosis, transplant rejection, rheumatoid arthritis, and psoriasis.

5. A therapeutically effective composition comprising a monoclonal anti-CD6 antibody, wherein the monoclonal antibody comprises heavy and light chain variable regions as set forth in Sequence ID No. 1 and 2, respectively, and in an amount to deliver a dose of 0.1-25 mg/Kg/week to a subject in need thereof, wherein the monoclonal antibody treats an auto-immune disorder in the subject selected from a group consisting of multiple sclerosis, transplant rejection, rheumatoid arthritis, and psoriasis and exhibits at least one of the following characteristics selected form the group consisting of:
   i does not induce complement dependent cytotoxicity (CDC), antibody dependent cytotoxicity or apoptosis in-vitro;
   ii inhibits naive T-cell proliferation by decreasing pro-inflammatory cytokines; and
   iii does not inhibit Memory-T-cell proliferation.

6. The monoclonal antibody of claim 1, wherein a dosage that effectively treats the auto-immune disorders is from 0.1-25 mg/Kg/week.

* * * * *